(12) United States Patent
Pugia

(10) Patent No.: US 8,632,990 B2
(45) Date of Patent: Jan. 21, 2014

(54) DETECTION OF SOLUBLE ADIPONECTIN RECEPTOR PEPTIDES AND USE IN DIAGNOSIS AND THERAPEUTICS

(75) Inventor: Michael Pugia, Granger, IL (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 74 days.

(21) Appl. No.: 13/326,380

(22) Filed: Dec. 15, 2011

(65) Prior Publication Data

US 2013/0149720 A1 Jun. 13, 2013

Related U.S. Application Data

(62) Division of application No. 12/096,076, filed as application No. PCT/US2006/061555 on Dec. 4, 2006, now Pat. No. 8,093,017.

(60) Provisional application No. 60/748,305, filed on Dec. 7, 2005.

(51) Int. Cl.
G01N 33/53 (2006.01)

(52) U.S. Cl.
USPC .................................................. 435/7.8

(58) Field of Classification Search
USPC .................................................. 435/7.8
See application file for complete search history.

(56) References Cited

U.S. PATENT DOCUMENTS

| 6,583,108 B1 | 6/2003 | Tamburini et al. |
| 6,858,402 B2 | 2/2005 | Gatanaga et al. |
| 2005/0032166 A1 | 2/2005 | Chan et al. |
| 2005/0245433 A1 | 11/2005 | Chan et al. |

FOREIGN PATENT DOCUMENTS

| EP | 1002865 | 5/2000 |
| JP | 2001-508648 | 7/2001 |
| WO | WO02/061076 | 8/2002 |
| WO | 02072149 | 9/2002 |
| WO | 03023008 | 3/2003 |
| WO | 2004022596 | 3/2004 |
| WO | 2004061108 | 7/2004 |
| WO | 2004063711 | 7/2004 |

OTHER PUBLICATIONS

Yamauchi et al. "Cloning of adiponectin receptors that mediate antidiabetic metabolic effects" Nature, 2003, 423:762-769.*
Arita, Y, et al."Paradoxical decrease of an adipose-specifica protein, adiponectin, in obesity" Bioche, Biophys Res Commun 1999, vol. 257, p. 79-83.
Hotta, K, et al., "Plasma concentration of a nove, adipose-specific protein,, adiponectin, in type 2 diabetic patients" Arterioscler Thromb Vac Biol, 2000, vol. 20, pp. 1595-1599.
Maeda, K. et al., "cDNA cloning and expression fof a novel adipose-specific collagen-like factor, apM1 (adipose most abundant gene transcript 1)" Biochem Biophys Res Cornmun 1996; vol. 221, pp. 288-289.
Hammana et al., "Normal adiponectin levels despite abnormal glucose tolerance (or diabetes) and inflammation in adult patients with cystic fibrosis", Diabetes & Metabolism, 2007, vol. 33 pp. 213-219.
Van der Poll et al. "Antiinflammatory cytokine responses during clinical sepsis and experimental endotoxemia sequential measurements of plasma soluble interleukin (IL)-1 receptor type II, IL-10 and IL-13", The Journal of Infectious Diseases 1997 vol. 175, pp. 118-122.
Chinetti, et al. "Expression of adiponectin receptors in human macrophages and regulation by agonists of the nuclear receptors PPARalpha, PPARgamma, and LXR" Biochemical and biophysical Research Communications, 2004. vol. 314 pp. 151-158.

* cited by examiner

Primary Examiner — Bin Shen
(74) Attorney, Agent, or Firm — Woodcock Washburn LLP; Kevin Stein

(57) ABSTRACT

The present invention relates to soluble C-terminal fragments of the adiponectin receptor and their use in the diagnosis and management of disorders.

24 Claims, No Drawings

DETECTION OF SOLUBLE ADIPONECTIN RECEPTOR PEPTIDES AND USE IN DIAGNOSIS AND THERAPEUTICS

CROSS REFERENCE TO RELATED APPLICATION

This application is a divisional of U.S. application Ser. No. 12/096,076, filed Feb. 23, 2006, now U.S. Pat. No. 8,093,017, which is the U.S. national stage of PCT/US2006/061555, filed Dec. 4, 2006, which claims the benefit of U.S. Provisional Application No. 60/748,305, filed Dec. 7, 2005.

FIELD

The present invention relates to soluble C-terminal fragments of the adiponectin receptor and their use in the diagnosis and management of disorders.

BACKGROUND OF THE INVENTION

Obesity with chronic inflammation has a large and growing population. This population clearly has a high cardiovascular and diabetes risk and frequently develops metabolic syndrome with insulin resistance. Recently adiponectin and other adipokines have been discovered as fat cell hormones that control glucose metabolism. Both type and location of fat cells are important. Obesity produces additional adipocytes which secrete adiponectin into the blood helping muscle cell metabolism of fats and glucose. Some overweight patients become insulin resistant. In this case, adipocytes stop producing adiponectin. Levels of adiponectin in the blood are decreased under conditions of obesity, insulin resistance and Type 2 diabetes. Methods exist for measuring adiponectin levels in subjects for the prognosis of these and other disease states. Measurement of adiponectin levels, however, has proven to be a weak indicator of disease. A need exists for better methods of monitoring disease states associated with abnormal adipocyte activity. The present invention provides this and other needs.

SUMMARY

The present inventors have discovered, that C terminal fragments of the adiponectin receptor are soluble and can be detected in bodily fluids. Accordingly, the present invention provides, among other thing, the fragments, methods of detecting them, methods of using them, and antibodies capable of binding to them.

Methods for detecting fragmentation of an adiponectin receptor in a biological fluid sample obtained from a subject can comprise the steps of assaying for the presence or absence of at least one soluble C-terminal fragment of the adiponectin receptor. In certain embodiments, the total concentration of C-terminal fragments in a biological sample is determined.

Methods for detecting the level of expression of an adiponectin receptor in a subject are provided herein. These methods can comprise the steps of determining the level of at least one C-terminal fragment of the adiponectin receptor in a biological fluid sample and correlating the level of the C-terminal fragment with the level of expression of the adiponectin receptor. In certain embodiments, the total concentration of C-terminal fragments in a biological sample is determined.

Methods for detecting the level of expression of adiponectin in a subject are provided herein. These methods can comprise the steps of determining the level of at least one C-terminal fragment of the adiponectin receptor in a biological fluid sample and correlating the level of the C-terminal fragment with the level of expression of adiponectin. In certain embodiments, the total concentration of C-terminal fragments in a biological sample is determined.

Methods for determining progression of a condition, onset of a condition, i.e., diagnosis, or efficacy of treatment, i.e., the responsiveness of and individual to therapy with a particular drug, are encompassed by the present invention. Preferably, the condition will be one associated with abnormal fragmentation patterns of an adiponectin receptor. These methods can comprise the steps of determining the level of at least one C-terminal fragment of the adiponectin receptor in a biological fluid sample and correlating the level of the C-terminal fragment with progression of the condition, onset of the condition, or efficacy of the treatment. In certain embodiments, the total concentration of C-terminal fragments in a biological sample is determined.

In the methods of the present invention, one or more (i.e., at least one) soluble C-terminal fragment of the adiponectin receptor can be detected. For example, any combination of fragments 1 to 22 of AdipoR1 and/or AdipoR2 can be detected. In certain embodiments, fragments 1 to 22 of AdipoR1 and/or AdipoR2 can be detected and differentiated by their masses. Accordingly, the present invention provide methods of determining the level of fragments having, for example, masses of from about 1 kDa to about 3 kDa, including, for example, a mass of about 2 kDa (e.g., fragments represented by SEQ ID NOS. 3, 12-22, 25, and 34-44) or fragments having masses of from about 3.5 to about 4.2 kDa, including for example a mass of about 3.9 kDa (e.g., fragments represented by SEQ ID NOS. 1, 2, 4-11, 23, 24 and 26-33). These size fragments are typically present as monomers. The present invention also provides methods of determining the level of fragments having, for example, masses of from about 2 kDA to about 6 kDA, including for example a mass of about 4 kDa or masses of about 7 kDa to about 8.4 kDa, including for example, a mass of about 7.8 kDa. These size fragments are typically present as dimers.

In the methods of the present invention, one or more soluble C-terminal fragment of the adiponectin receptor (e.g., SEQ ID NOS. 1-44) can be detected when bound to a carrier protein. For example, any combination of fragments 1 to 22 of AdipoR1 and/or AdipoR2 can be detected when attached to a carrier protein. Accordingly, in certain embodiments, the present invention provide methods of determining the level of fragments having masses of about 4.5-6.9, 7-8.2, 9-11, 13-15, 17-19, 27-29, or 30-34, kDa. In certain embodiments, the carrier protein is adiponectin, including adiponectin fragments. In certain embodiments, the combined adiponectin receptor fragment with bound adiponectin has a mass of about 3-5, 4-8, 7-11, 13-17, 22-26 or 28-32 kDa. The present invention provides methods of detecting these fragments.

The present invention also provides polypeptides that are substantially identical to fragments having the sequences of SEQ ID NOs: 1 to 44 and the nucleic acid sequences that correspond to these fragments. Antibodies that specifically bind to at least one of the C-terminal fragments of the adiponectin receptor provided herein are also included.

The present invention provides a kit for use in determining treatment strategy for an individual with any of the disorders described herein comprising a means for detecting at least one of the fragments described herein; and optionally instructions for use and interpretation of the kit results. The kit can also comprise, for example, a means for obtaining a biological sample from an individual.

DETAILED DESCRIPTION OF ILLUSTRATIVE EMBODIMENTS

I. Introduction

The present inventors have discovered, that C terminal fragments of the adiponectin receptor are soluble and can be detected in bodily fluids. Moreover, the present inventors have observed that the presence or absence of certain soluble fragments of the adiponectin receptor in bodily fluids is predictive of disease and that the level, i.e., concentration, of total soluble adiponectin receptor fragments in the bodily fluid is predictive of disease.

It is to be understood that the invention described herein is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

II. Adiponectin Receptor and Fragments Thereof.

The adiponectin receptor is a transmembrane receptor that was first described by Yamauchi et al., (Nature, 2003, 423 (6941), 762-9) and has several types. Three adiponectin receptor types have been identified, adiponectin receptor 1 (also referred to as AdipoR1), adiponectin receptor 2 (also referred to as AdipoR2) and adiponectin receptor 3 (also referred to as AdipoR3). Adiponectin receptors specifically bind to and are modulated by adiponectin, an adipocyte-derived factor that plays a significant role in lipid and glucose metabolism in the muscle and liver.

The nucleic acid and amino acid sequence of human adiponectin receptors 1 and 2 are accessible in public databases (e.g., see Genbank accession numbers NM_015999, AK222503, AK025085, AK222503, NM_024551, Q96A54, and Q86V24) and are provided herein. The nucleic acid and amino acid sequences of human adiponectin receptor 3 is provided in U.S. Publication No. 20050032166, incorporated herein by reference in its entirety. It will be understood that the term adiponectin receptor, as used herein, not only encompasses adiponectin receptors having the sequences described herein but also includes, for example, naturally-occurring truncated forms of an adiponectin receptor, naturally-occurring variant forms (e.g., alternatively spliced forms), conservatively modified variants, and naturally-occurring allelic variants.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The phrase "soluble C terminal fragments of the adiponectin receptor" refers to fragments from the C terminus of the adiponectin receptor that break off from the adiponectin receptor and are soluble in bodily fluids. A variety of bodily fluids can be used in practicing the methods of the invention including, for example, blood, serum, plasma, urine, salivary fluid, ascite fluid and the like.

Adiponectin is well known in the art as a hormone secreted by adipocytes having insulin-sensitizing, antiatherogenic, and antiinflammatory properties. Levels of adiponectin are decreased under certain conditions, including obesity, insulin resistance and diabetes. The activity of adiponectin is mediated by its receptors. Adiponectin can exist as a full-length or as a smaller globular fragment. There are four distinct regions of adiponectin. The first is a short signal sequence that targets the hormone for secretion outside the cell, next is a short region that varies between species; the third is a region with similarity to collagenous proteins; and the last is a globular domain. The predicted monomeric mass for adiponectin is 26 kDa with a range of from about 17 to about 33 kDa. Oligomer formation of adiponectin depends on disulfide bond formation mediated by an internal cysteine residue. Adiponectin exists in a wide range of multimer complexes in plasma and combines via its collagen domain to create 3 major oligomeric forms: a low, middle and high molecular weight form.

Serine proteases such as elastase and trypsin have multiple sites for cleaving adiponectin. A release of globular adiponectin at an average molecular weight of about 16 kDa is known to occur in patients. The remaining non-globular adiponectin has an average molecular weight of 10 kDA. The cleavage of adiponectin by a trypsin type serine protease can occur, for example, at amino acid 101 causing a 16.5 kDA globular adiponectin or by an elastase type serine protease at amino acid 108 causing a 15.8 kDa globular adiponectin. There are multiple potential cleavage sites in amino acid 88 to 108 causing a mass range for globular adiponectin of between about 17.8 kDa to about 9.7 kDa. Additional protease cleavage of non-globular adiponectin can produce fragments as small as 3 kDa.

Without wishing to be bound by theory, it is believed that the c-terminal tail of the adiponectin receptor acts to capture full length adiponectin. The binding is believed to occur between the non-globular portion of the adiponectin protein and the adiponectin tail binding domain of the adiponectin receptor. After cleavage by the protease, the non-globular adiponectin is believed to remain bound to the c-terminal region of the adiponectin receptor. The freed globular adiponectin is thought to interact with another region on the receptor to cause further activation. In the absence of non-globular adiponectin, binding to the c-terminal is not believed to occur.

The present inventors have discovered that the C-terminal portion of the adiponectin receptor fragments off the receptor and is present in bodily fluid. The presence or level of non-globular adiponectin can impact the fragmentation pattern for the c-terminal of the adiponectin receptor. The present inventors have detected fragments of adiponectin receptor 1 and 2 in bodily fluid. The observation and conclusion that the adiponectin receptor can be detected in biological fluid and provide a reliable and practical indicator of disease states is particularly surprising given the fact that the adiponectin receptor is an integral membrane protein. It is also surprising that certain fragments tend to be absent in disease and that increase in the total number or concentration of receptor fragments occurs in disease states, given that adiponectin levels decreases with disease.

The present invention provides, inter alia, adiponectin receptor fragments 1 to 22 (SEQ ID NOS:1-22) of AdipoR1. Fragment 1 of AdipoR1 has 34 amino acids corresponding to amino acids 361 to 375 on AdipoR1 Amino acids 1-14 is the serine protease cleavage domain; amino acids 15-22 is the adipoR2-like domain; and amino acids 23-34 are the adiponectin binding domain. The sequence of fragment 1 of AdipoR1 is vlvvaaafvh fygvsnlqef rygleggctd dtll (SEQ ID NO:1). This fragment can be further fragmented at any amino acid, and, in particular, at any amino acid within the serine protease cleavage domain, adipoR1-like domain, or adiponectin binding domain. Certain key fragments present in bodily fluid are fragment 2 with a sequence of lvvaaafvh fygvsnlqef rygleggctd dtll (SEQ ID NO:2) and fragment 3 with a sequence of snlqef rygleggctd dtll (SEQ ID NO:3) but at least the following fragments can be found: vvaaafvh fygvsnlqef rygleggctd dtll (SEQ ID NO:4), vaaafvh fygvsnlqef rygleggctd dtll (SEQ ID NO:5), aaafvh fygvsnlqef rygleggctd dtll (SEQ ID NO:6), aafvh fygvsnlqef rygleggctd dtll (SEQ ID NO:7), afvh fygvsnlqef rygleggctd dtll (SEQ ID NO:8), fvh fygvsnlqef rygleggctd dtll (SEQ ID NO:9), vh fygvsnlqef rygleggctd dtll (SEQ ID NO:10), h fygvsnlqef rygleggctd dtll (SEQ ID NO:11), fygvsnlqef rygleggctd dtll (SEQ ID NO:12), ygvsnlqef rygleggctd dtll (SEQ ID NO:13), gvsnlqef rygleggctd dtll (SEQ ID NO:14), vsnlqef rygleggctd dtll (SEQ ID NO:15), nlqef rygleggctd dtll (SEQ ID NO:16), lqef rygleggctd dtll (SEQ ID NO:17), qef rygleggctd dtll (SEQ ID NO:18), of rygleggctd dtll (SEQ ID NO:19), f rygleggctd dtll (SEQ ID NO:20), rygleggctd dtll (SEQ ID NO:21), and ygleggctd dtll (SEQ ID NO:22).

The present invention provides, inter alia, adiponectin receptor fragments 1 to 22 (SEQ ID NOS:23-44) of AdipoR2. Fragment 1 of AdipoR2 has 34 amino acids corresponding to amino acids 353 to 386 on AdipoR2 Amino acids 1-14 is the serine protease cleavage domain; amino acids 15-22 is the adipoR2-like domain; and amino acids 23-34 are the adiponectin binding domain. The sequence of fragment 1 of AdipoR2 is ifvvagafvh fhgvsnlqef rfmigggcse edal (SEQ ID NO:23). This fragment can be further fragmented at any amino acid, and, in particular, at any amino acid within the serine protease cleavage domain, adipoR2-like domain, or adiponectin binding domain. The key fragments present in bodily fluid are fragment 2 with a sequence of vagafvh fhgvsnlqef rfmigggcse edal (SEQ ID NO:24) and fragment 3 with a sequence of snlqef rfmigggcse edal (SEQ ID NO:25) but at least the following fragments can also be found: fvvagafvh fhgvsnlqef rfmigggcse edal (SEQ ID NO:26), vvagafvh fhgvsnlqef rfmigggcse edal (SEQ ID NO:27), agafvh fhgvsnlqef rfmigggcse edal (SEQ ID NO:28), gafvh fhgvsnlqef rfmigggcse edal (SEQ ID NO:29), afvh fhgvsnlqef rfmigggcse edal (SEQ ID NO:30), fvh fhgvsnlqef rfmigggcse edal (SEQ ID NO:31), vh fhgvsnlqef rfmigggcse edal (SEQ ID NO:32), h fhgvsnlqef rfmigggcse edal (SEQ ID NO:33), fhgvsnlqef rfmigggcse edal (SEQ ID NO:34), hgvsnlqef rfmigggcse edal (SEQ ID NO:35), gvsnlqef rfmigggcse edal (SEQ ID NO:36), vsnlqef rfmigggcse edal (SEQ ID NO:37), nlqef rfmigggcse edal (SEQ ID NO:38), lqef rfmigggcse edal (SEQ ID NO:39), qef rfmigggcse edal (SEQ ID NO:40), of rfmigggcse edal (SEQ ID NO:41), f rfmigggcse edal (SEQ ID NO:42), rfmigggcse edal (SEQ ID NO:43), and fmigggcse edal (SEQ ID NO:44).

In certain instances, the adiponectin receptor present in the body does not have the exact sequence as described herein but is present as a naturally occurring variant form. For example, the adiponectin receptors can substitute at least up to 5% or even up to 10% of their amino acids without having a loss of function. Accordingly, at least a couple of the amino acids in SEQ ID NOS. 1 to 44 can be substituted with other amino acids. Accordingly, the present invention encompasses not only fragments 1-22 of AdipoR1 and AdipoR2 but also fragments having substantial identity to the fragments described herein. Substantial identity is described herein as having about 75% or 80% or greater identity to the fragments. Accordingly, the fragments can have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% to SEQ ID NOS 1 to 44.

Percent identity can be determined by comparing two optimally aligned sequences over a comparison window, wherein the portion of the polypeptide sequence in the comparison window can comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Identity is evaluated using any of the variety of sequence comparison algorithms and programs known in the art. Such algorithms and programs include, but are by no means limited to, TBLASTN, BLASTP, FASTA, TFASTA, CLUSTALW, FASTDB, the disclosures of which are incorporated by reference in their entireties. Pearson, et al., Proc. Natl. Acad. Sci. U.S.A., 85: 2444-2448, 1988; Altschul, et al., J. Mol. Biol., 215: 403410, 1990; Thompson, et al., Nucleic Acids Res., 22: 4673-4680, 1994; Higgins, et al., Meth. Enzymol., 266: 383402, 1996; Altschul, et al., Nature Genetics, 3: 266-272, 1993; Brutlag, et al., Comp. App. Biosci., 6: 237-24, 1990.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

As used herein, the term "polynucleotide" means a polymeric form of nucleotides of at least about 10 bases or base pairs in length, either ribonucleotides or deoxynucleotides or a modified form of either type of nucleotide, and is meant to include single and double stranded forms of DNA.

The adiponectin receptor fragments described herein can dimerize through the cysteine amino acid present near the c terminal of the fragment (position 28 in SEQ ID NO:1 and 16). Accordingly, these fragments can be present in the bodily fluid as dimers.

Several of the amino acids present in SEQ ID NOS: 1-44 are potential sites for post-translational modification. For example, the glycine present in the fragments (position 26 in SEQ ID NO:1 and 23) is a potential N-myristoylation site, the arginine (position 21 in SEQ ID NO:1 and 23) is a potential N-glycan site and the serine (position 15 in SEQ ID NO:1 and 23) is a potential O-glycan site. Accordingly, the fragments may have additional mass due to post-translational modifications.

One aspect of the present invention is the provision of the fragments described herein. Accordingly, the present invention provides isolated fragments having substantial identity to SEQ ID NOS:1-44. Isolated fragments are those that have been purified from a biological source or have been prepared by recombinant or synthetic methods. Methods of doing so are well known in the art and are thus, not described herein.

Another aspect of the present invention is the detection of the fragments described herein in a biological fluid sample.

The present inventors have discovered that fragments of the adiponectin receptor, a transmembrane receptor, can be detected in biological fluid sample by assaying for the presence of a c-terminal region of the receptor in the biological fluid.

It has also been discovered that the level of expression of the adiponectin receptor in tissue can be determined by determining the level of at least one C-terminal fragment of the adiponectin receptor in a biological fluid sample and comparing the level of the at least one C-terminal fragment to the level of the same fragment in a control sample.

It has also been discovered that the level of expression of adiponectin in a subject can be determined by determining the level of at least one C-terminal fragment of the adiponectin receptor in a biological fluid sample and comparing the level of the at least one C-terminal fragment to the level of the same fragment in a control sample Fragments of the adiponectin receptor can be found in the bodily fluids of diseased and non-diseased individuals. The presence or level of adiponectin, however, can impact the fragmentation pattern for the c-terminal of the adiponectin receptor. The levels and type of adiponectin in a subject can also impact the levels of adiponectin receptor present in the subject.

The present inventors have discovered that in normal subjects (i.e., non-diseased) having normal levels of full-length adiponectin, larger adiponectin receptor fragments are found in the biological fluids, i.e., fragments that are 25 to 34 amino acid in length (i.e., SEQ ID NOS: 1, 2, 4-11, 23, 24, and/or 26-33). These fragments are typically unbound. Many of these larger fragments are absent or present in significantly lower levels in subjects suffering from adiponectin related disease (i.e., fragments are present in diseased patients at levels 2×, 5×, 10×, 20×, 50×, 100× less, or more than 100× less than in non-diseased patients). By unbound fragments, it is meant fragments that are not bound to carrier protein, i.e., adiponectin.

The present inventors have discovered that in diseased subjects, smaller adiponectin fragments are found in the biological fluids, i.e., fragments that are about 13 to 24 amino acids in length (i.e., SEQ ID NOS: 3, 12-22, 25, and/or 34-44). These fragments can be bound or unbound. These fragments are also found in normal subjects but generally not at the same levels as in diseased subjects (i.e., fragments are present in diseased patients at levels 1.5×, 2×, 2.5×, 4×, 5×, 6×, 7×, 8×, 9×, or 10× more than in non-diseased patients).

The present inventors have found that in both normal and diseased subjects, c-terminal adiponectin receptor fragments bound to adiponectin are observed. These bound receptor fragments can be the larger or smaller fragments. In many cases these fragments were bound to the non-globular portion of adiponectin whether partially fragmented or full length. The level of bound adiponectin receptor fragments is increased in subjects with disease.

The presence and/or levels of the unbound and bound fragments and smaller and larger fragments can, accordingly, be used to determine the level of expression of adiponectin and the adiponectin receptor in an individual as well as disease states in individuals.

III. Detection of Soluble C Terminal Fragments of the Adiponectin Receptor

The present invention provides methods for assaying for the presence or absence and/or determining the level of at least one soluble C terminal fragment of the adiponectin receptor in bodily fluid. The phrase "determining the level" means detecting the presence or absence of an analyte in a sample or quantifying the amount in relative or absolute terms. A relative amount could be, for example, high, medium or low. An absolute amount could reflect the measured strength of a signal or the translation of this signal strength into another quantitative format, such as micrograms/ml.

The C terminal fragments can be detected by any suitable method. Detection paradigms that can be employed include, for example, optical methods, electrochemical methods (voltametry and amperometry techniques), atomic force microscopy, and radio frequency methods, e.g., multipolar resonance spectroscopy. Optical methods include, for example, colorimetric assays, electron impedance spectroscopy, microscopy, both confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In certain preferred embodiments, the level of expression, including presence or absence of at least one soluble C terminal fragment of the adiponectin receptor is assayed by an immunoassay. Those skilled in the art are aware that, in its broadest context, an "immunoassay" comprises incubating a test sample with one or more immunointeractive molecules specific for a target for a time and under conditions sufficient for binding thereto and detecting said binding. As used herein, the term "target" refers to the analyte which a probe is designed to bind. In certain preferred embodiments, the immunointeractive molecule will be an antibody. Conditions for incubating an antibody with a test sample vary, depending upon the format employed in the assay, the detection methods employed and the type and nature of the antibody molecule used in the assay. Those skilled in the art will recognize that any one of the commonly available immunological assay formats, for example radioimmunoassay, enzyme-linked immunosorbent assays (ELISA), immuno-tubimetric, immunonephrometric, magnetic immuno particle separation, immunochromatography, immuno-microfludic, immunocentrifugal, diffusion-based Ouchterlony, rocket gel immunoelectrophoresis or in situ immunoassays can be readily adapted to the present purpose.

Immunoassays are useful in the quantification of at least one soluble C terminal fragment of the adiponectin receptor in a test sample, in particular to determine whether the level of the at least one soluble C terminal fragment is altered compared to normal levels detectable in non-diseased individuals. As a consequence, such an immunoassay is of particular use in determining whether a patient may have a disease or predisposition to disease. The immunoassay can have other uses as well, such as, for example, use in the monitoring of disease progression or monitoring of response to therapeutic interventions. The invention described herein extends to all such uses of immunointeractive molecules and diagnostic assays which require said immunoassays for their performance.

By way of example only, in certain embodiments, an antibody raised against the fragment is immobilised onto a solid substrate to form a first complex and a biological test sample from a patient is brought into contact with the bound molecule. After a suitable period of incubation, for a period of time sufficient to allow formation of an antibody-secondary complex, a second antibody labeled with a reporter molecule capable of producing a detectable signal is then added and incubated, allowing sufficient time for the formation of a tertiary complex. Any unreacted material is washed away, and the presence of the tertiary complex is determined by observation of a signal produced by the reporter molecule. The results can either be qualitative, by simple observation of the visible signal or may be quantitated by comparison with a control sample containing known amounts of hapten. Variations of this assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, and the possibility of variations will be readily apparent.

By "reporter molecule", as used in the present specification, is meant a molecule which, by its chemical nature, produces an analytically identifiable signal which allows the detection of antigen-bound antibody. Detection can be either qualitative or quantitative. The most commonly used reporter molecule in this type of assay are either colored latex particles, metal particles, enzymes, fluorophores or radionuclide containing molecules (i.e. radioisotopes)

The solid substrate is typically glass or a polymer, the most commonly used polymers being cellulose, polyacrylamide, nylon, nitrocellulose, polystyrene, polyvinyl chloride or polypropylene. The solid supports may be in the form of strips, cassettes, tubes, beads, discs or microplates, or any other surface suitable for conducting an immunoassay. The binding processes are well-known in the art and generally consist of cross-linking covalently binding or physically adsorbing the molecule to the insoluble carrier.

A variety of immunoassay formats, including, for example, competitive and non-competitive immunoassay formats, antigen capture assays and two-antibody sandwich assays can be used in the methods of the invention (Self and Cook, *Curr. Opin. Biotechnol.* 7:60-65 (1996)). In an antigen capture assay, antibody is bound to a solid phase, and sample is added such that a soluble adiponectin receptor C terminal fragment antigen is bound by the antibody. The antibody can be specific for one or two or more of the soluble C terminal fragments. After unbound proteins are removed by washing, the amount of bound antigen can be quantitated, if desired, using, for example, a radioassay (Harlow and Lane, *Antibodies A Laboratory Manual* Cold Spring Harbor Laboratory: New York, 1988)) Immunoassays can be performed under conditions of antibody excess, or as antigen competitions, to quantitate the amount of antigen and, thus, determine a level of soluble adiponectin receptor C terminal fragments.

Enzyme-linked immunosorbent assays (ELISAs) can be useful in certain methods of the invention. In the case of an enzyme immunoassay, an enzyme is conjugated to the second antibody, generally by means of glutaraldehyde or periodate. As will be readily recognised, however, a wide variety of different conjugation techniques exist which are readily available to one skilled in the art. Commonly used enzymes include, for example, horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. It is also possible to employ fluorogenic substrates, for example, which yield a fluorescent product. An enzyme such as horseradish peroxidase (HRP), alkaline phosphatase (AP), β-galactosidase or urease can be linked, for example, to an anti-adiponectin receptor C terminal fragment or to a secondary antibody for use in a method of the invention. A horseradish-peroxidase detection system can be used, for example, with the chromogenic substrate tetramethylbenzidine (TMB), which yields a soluble product in the presence of hydrogen peroxide that is detectable at 450 nm. Other convenient enzyme-linked systems include, for example, the alkaline phosphatase detection system, which can be used, for example, with the chromogenic substrate p-nitrophenyl phosphate to yield a soluble product readily detectable at 405 nm. Similarly, a β-galactosidase detection system can be used with, for example, the chromogenic substrate o-nitrophenyl-β-D-galactopyranoside (ONPG) to yield a soluble product detectable at 410 nm, or a urease detection system can be used with, for example, a substrate such as urea-bromocresol purple (Sigma Immunochemicals, St. Louis, Mo.). Useful enzyme-linked primary and secondary antibodies can be obtained from a number of commercial sources such as Jackson Immuno-Research (West Grove, Pa.).

In certain embodiments, the soluble C terminal fragments can be detected and measured using chemiluminescent detection. For example, in certain embodiments, adiponectin receptor C terminal fragment specific antibodies are used to capture the fragments present in the biological sample and a antibody specific for the specific antibodies and labeled with an chemiluminescent label is used to detect the fragments present in the sample. Any chemiluminescent label and detection system can be used in the present methods. Chemiluminescent secondary antibodies can be obtained commercially from various sources such as Amersham. Methods of detecting chemiluminescent secondary antibodies are known in the art and are not discussed herein in detail.

Fluorescent detection also can be useful for detecting the adiponectin receptor fragments in certain methods of the invention. Useful fluorochromes include, for example, DAPI, fluorescein, lanthanide metals, Hoechst 33258, R-phycocyanin, B-phycoerythrin, R-phycoerythrin, rhodamine, Texas red and lissamine Fluorescein or rhodamine labeled α2-MG-, HA-, TIMP-1- or YKL-40-specific binding agents such as anti-α2-MG, anti-HA, anti-TIMP-1, or anti-YKL-40 antibodies, or fluorescein- or rhodamine-labeled secondary antibodies can be useful in the invention. Useful fluorescent antibodies can be obtained commercially, for example, from Tago Immunologicals (Burlingame, Calif.) as described further below. Fluorescent compounds, can be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope.

Radioimmunoassays (RIAs) also can be useful in certain methods of the invention. Such assays are well known in the art. Radioimmunoassays can be performed, for example, with $^{125}$I-labeled primary or secondary antibody (Harlow and Lane, supra, 1988).

A signal from a detectable reagent can be analyzed, for example, using a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of soluble adiponectin receptor fragments can be performed using a spectrophotometer such as an EMAX Microplate Reader (Molecular Devices; Menlo Park, Calif.) in accordance with the manufacturer's instructions. The assays of the invention can be automated or performed robotically, if desired, and that the signal from multiple samples can be detected simultaneously.

The methods of the invention also encompass the use of capillary electrophoresis based immunoassays (CEIA), which can be automated, if desired Immunoassays also can be used in conjunction with laser-induced fluorescence as described, for example, in Schmalzing and Nashabeh, *Electrophoresis* 18:2184-93 (1997), and Bao, *J. Chromatogr. B. Biomed. Sci.* 699:463-80 (1997). Liposome immunoassays, such as flow-injection liposome immunoassays and liposome immunosensors, also can be used to detect soluble C terminal adiponectin fragments or to determine a level of C terminal adiponectin fragments according to certain methods of the invention (Rongen et al., *J. Immunol. Methods* 204:105-133 (1997)).

Sandwich enzyme immunoassays also can be useful in certain methods of the invention. In a two-antibody sandwich assay, a first antibody is bound to a solid support, and the antigen is allowed to bind to the first antibody. The amount of soluble C terminal adiponectin fragments can be quantitated by measuring the amount of a second antibody that binds to it.

Quantitative western blotting also can be used to determine a level of soluble C terminal adiponectin fragments in a method of the invention. Western blots can be quantitated by well known methods such as scanning densitometry. As an example, protein samples are electrophoresed on 10% SDS-PAGE Laemmli gels. Primary murine monoclonal antibodies are reacted with the blot, and antibody binding confirmed to be linear using a preliminary slot blot experiment. Goat anti-mouse horseradish peroxidase-coupled antibodies (BioRad) are used as the secondary antibody, and signal detection performed using chemiluminescence, for example, with the Renaissance chemiluminescence kit (New England Nuclear; Boston, Mass.) according to the manufacturer's instructions. Autoradiographs of the blots are analyzed using a scanning densitometer (Molecular Dynamics; Sunnyvale, Calif.) and normalized to a positive control. Values are reported, for example, as a ratio between the actual value to the positive control (densitometric index). Such methods are well known in the art as described, for example, in Parra et al., *J. Vasc. Surg.* 28:669-675 (1998).

Levels of adiponectin receptor fragments can also be determined using protein microarrays. Methods of producing protein microarrays that may be adapted for detecting levels of protein in a clinical sample are described in the art (see for example of Xiao et al. (2005) Mol Cell Endocrinol.; 230(1-2):95-10; Protein Microarrays (2004) Mark Schena (Ed) Jones & Bartlett Publishers, Inc.). U.S. patent Pub. 2003/0153013 describes methods of detecting proteins, e.g. antigens or antibodies, by immobilizing antibodies in a protein microarray on a membrane and contacting the microarray with detection proteins which can bind to the proteins to form protein complexes. Similarly, U.S. patent Pub. 2004/0038428 describes methods of constructing protein microarrays.

In certain preferred embodiments, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of peptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications:

U.S. Pat. No. 6,225,047; PCT International Publication No. WO 99/51773; U.S. Pat. No. 6,329,209, PCT International Publication No. WO 00/56934 and U.S. Pat. No. 5,242,828, incorporated herein by reference in their entirety and for all purposes.

For use herein, the assay methods can involve capturing the C-terminal adiponectin receptor fragments onto a solid substrate. Typically they will be captured using a biospecific capture reagent such as an antibody and, in particular, an antibody used in an immunoassay. Biospecific capture reagents include those molecules that bind a target analyte with an affinity of, for example, at least $10^{-9}$ M, $10^{-19}$ M, $10^{-11}$ M or $10^{-12}$ M. These molecules also can be captured with non-specific methods, such as chromatographic materials.

In certain embodiments of the present invention, at least one C terminal fragment of the adiponectin receptor will be detected by mass spectrometry. Examples of mass spectrometers are time-of-flight, magnetic sector, quadrupole filter, ion trap, ion cyclotron resonance, electrostatic sector analyzer and hybrids of these.

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip, each of which is incorporated herein by reference in its entirety and for all purposes. This refers to a method of desorption/ionization gas phase ion spectrometry (e.g., laser desorption/ ionization mass spectrometry) in which an analyte is captured on the surface of a SELDI probe that engages the probe interface of the mass spectrometer.

One version of SELDI is called "affinity mass spectrometry." This version involves the use of probes comprising of an absorbent surface (an "affinity mass spectrometry probe"). In this context, "probe" refers to a device adapted to engage a probe interface and to present an analyte to ionizing energy for ionization and introduction into a mass spectrometer. A probe typically includes a solid substrate, either flexible or rigid, that has a sample-presenting surface, on which an analyte is presented to the source of ionizing energy.

Another version of SELDI is Surface-Enhanced Neat Desorption ("SEND"), which involves the use of probes comprising energy absorbing molecules attached to the probe surface ("SEND probe"). The phrase "Energy absorbing molecules" (EAM) denotes molecules that are capable of absorbing energy from a laser desorption/ionization source and, thereafter, contributing to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy-absorbing molecule is incorporated into a linear or cross-linked polymer, e.g., a polymethacrylate. For example, the composition can be a co-polymer of a-cyano-4-methacryloyloxycinnamic acid and acrylate. In another embodiment, the composition is a co-polymer of a-cyano-4-methacryloyloxycinnamic acid, acrylate and 3-(tri-ethoxy)silyl propyl methacrylate. In another embodiment, the composition is a co-polymer of a-cyano-4-methacryloyloxycinnamic acid and octadecyl-methacrylate ("C18 SEND"). SEND is further described in U.S. Pat. No. 6,124,137, incorporated herein by reference in its entirety and for all purposes.

A "selective surface" can be used to capture the fragments for SELDI analysis. The selective surface has an "adsorbent," also called a "binding moiety" or "capture reagent" attached to the surface. An "adsorbent" or "capture reagent" or "binding moiety," can be any material capable of binding an analyte. The capture reagent can be attached directly to the substrate of the selective surface, or the substrate can be a "reactive surface" that carries a "reactive moiety" that is capable of binding the capture reagent, e.g., through a reaction forming a covalent or coordinate covalent bond. Epoxide and carbodiimidazole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides.

In certain embodiments, the adsorbent used to capture the C-terminal adiponectin receptor fragments comprises a biospecific capture reagent. A "biospecific adsorbent" refers to an adsorbent that binds to an analyte with an affinity of at least $10^{-9}$ M, $10^{-10}$ M, $10^{-11}$ M or $10^{-12}$ M. The preferred biospecific capture reagent is an antibody or a binding fragment thereof. This includes intact immunoglobulins and the variants and portions of them well known in the art such as, Fab' fragments, F(ab)'2 fragments, and scFv proteins. Other biospecific capture reagents include affibodies (Affibody, Teknikringen 30, floor 6, Box 700 04, Stockholm SE-10044, Sweden, U.S. Pat. No. 5,831,012; see also Surface Logix, Inc., 50 Soldiers Field Place, Brighton, Mass. 02135 and Hodneland, C. D, et al., 2002, Proc. Natl. Acad. Sci. 99: 5048-5052)

The fragments of the present invention can be captured on chromatographic adsorbents. "Chromatographic adsorbent" refers to an adsorbent material typically used in chromatography. Chromatographic adsorbents include, for example, nitrocellulose membranes, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

In certain embodiments, a substrate with an adsorbent is contacted with the sample, e.g., patient serum, for a period of time sufficient to allow the target analytes that may be present to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties, an energy absorbing molecule then is applied to the substrate with the bound target analytes.

The biomolecules bound to the substrates can be detected in a gas phase ion spectrometer such as a time-of-flight mass spectrometer. The target analytes can be ionized by an ionization source such as a laser, the generated ions are collected by an ion optic assembly, and then a mass analyzer disperses and analyzes the passing ions. The detector then translates information of the detected ions into mass-to-charge ratios. Detection of a target analyte typically will involve detection of signal intensity. Thus, both the quantity and mass of the target analyte can be determined.

In another mass spectrometry method, the target analytes can be first captured on a chromatographic resin having chromatographic properties that bind the target analytes, e.g., an antibody or antibodies. In the present example, this can include an immuno-chromatographic resin that comprises antibodies that bind C-terminal adiponectin receptor fragments. Unbound material can be washed from the resin. Then the target analytes can be eluted from the resin. Finally, the eluted target analytes can be detected by MALDI or by SELDI.

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing.

Data generated by desorption and detection of target analytes can be analyzed with the use of a programmable digital computer. The computer program analyzes the data to indicate the number of proteins detected, and optionally the strength of the signal and the determined molecular mass for each target analyte detected. Data analysis can include steps of determining signal strength of a target analyte and removing data deviating from a predetermined statistical distribution. For example, the observed peaks can be normalized, by calculating the height of each peak relative to some reference. The reference can be background noise generated by the instrument and chemicals such as the energy absorbing molecule which is set as zero in the scale.

Analysis generally involves the identification of peaks in the spectrum that represent signal from an analyte. Peak selection can be done visually, but software is available that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a target analyte according to the present invention. The software also can subject the data regarding observed target analyte peaks to classification tree or ANN analysis, to determine whether a target analyte peak or combination of target analyte peaks is present that indicates cardiovascular disease status. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

IV. Antibodies

This invention further provides antibodies that specifically bind to the C-terminal fragments of the adiponectin receptor. Methods of making antibodies having binding specificity to select peptides are well known in the art. For example, such antibodies can be selected by immunizing an animal with the target molecule, generating antibodies, and testing the antibodies to identify whether a particular antibody binds with the target molecule. Antibodies that bind with the target molecule can be selected. For example, one can generate monoclonal antibodies against these molecules.

The phrase "specifically binds to" refers to a binding reaction which is determinative of the presence of a target in the presence of a heterogeneous population of other biologics. Thus, under designated assay conditions, the specified binding region bind preferentially to a particular target and do not bind in a significant amount to other components present in a test sample. Specific binding to a target under such conditions can require a binding moiety that is selected for its specificity for a particular target. A variety of assay formats can be used to select binding regions that are specifically reactive with a particular analyte. Typically a specific or selective reaction will be at least twice background signal or noise and more typically more than 10 times background.

The term "antibody" is used in the broadest sense and specifically covers monoclonal antibodies, polyclonal antibodies, antibody compositions with polyepitopic specificity, bispecific antibodies, diabodies, chimeric, single-chain, and humanized antibodies, as well as antibody fragments (e.g., Fab, F(ab')$_2$, and Fv), so long as they exhibit the desired biological activity. Antibodies can be labeled for use in biological assays (e.g., radioisotope labels, fluorescent labels) to aid in detection of the antibody.

Antibodies can be labeled/conjugated to reporter molecules for use in biological assays (e.g., radioisotope labels, fluorescent labels) to aid in detection of the fragments described herein.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler, et al., Nature, 256: 495, 1975, or can be made by recombinant DNA methods (see, e.g., U.S. Pat. No. 4,816,567, Cabilly, et al.). The "monoclonal antibodies" can also be isolated from phage antibody libraries using the techniques described in Clackson, et al., 624-628, 1991; Marks, et al., J. Mol. Biol., 222: 581-597, 1991, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly, et al., supra; Morrison, et al., Proc. Natl. Acad. Sci. U.S.A., 81: 6851-6855, 1984).

Monoclonal antibodies can be obtained by various techniques familiar to those skilled in the art. Briefly, spleen cells from an animal immunized with a desired antigen are immortalized, commonly by fusion with a myeloma cell (see, Kohler, et al., Eur. J. Immunol., 6: 511-519, 1976). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse, et al., Science, 246: 1275-1281, 1989.

Monoclonal antibodies and polyclonal sera can be collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones, et al., *Nature,* 321: 522-525, 1986; Reichmann, et al., *Nature,* 332: 323-329, 1988; Presta, *Curr. Op. Struct. Biol.,* 2: 593-596, 1992. The humanized antibody includes a Primatized™ antibody wherein the antigen-binding region of the antibody is derived from an antibody produced by immunizing macaque monkeys with the antigen of interest.

A number of immunogens comprising portions of the fragments described herein can be used to produce antibodies specifically reactive with the fragments. For example, a fragment of the present invention, can be isolated using techniques known in the art. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein can also be used either in pure or impure form. The product is then injected into an animal capable of producing antibodies. Either monoclonal or polyclonal antibodies can be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

In a further embodiment, antibodies or antibody fragments can be isolated from antibody phage libraries generated using the techniques described in McCafferty, et al., *Nature,* 348: 552-554, 1990; Clackson, et al., *Nature,* 352: 624-628, 1991; Marks, et al., *J. Mol. Biol.,* 222: 581-597, 1991, describe the isolation of murine and human antibodies, respectively, using phage libraries. Subsequent publications describe the production of high affinity (nM range) human antibodies by chain shuffling (Mark, et al., *Bio/Technology,* 10: 779-783, 1992), as well as combinatorial infection and in vivo recombination as a strategy for constructing very large phage libraries (Waterhouse, et al., *Nuc. Acids. Res.,* 21: 2265-2266, 1993). Thus, these techniques are viable alternatives to traditional monoclonal antibody hybridoma techniques for isolation of monoclonal antibodies.

In certain embodiments, the antibodies are selected to distinguish between one fragment of C-terminal adiponectin receptor and another, that is, the antibodies are selected that specifically bind to one form, but not another, under the same assay conditions.

Accordingly, the present invention provides an antibody that specifically binds to an epitope of an adiponectin receptor fragment having SEQ ID NO:1. In certain embodiments, the antibody will specifically bind to a region of SEQ ID NO:1 that is outside of the adiponectin binding domain, i.e., the antibody will specifically bind to an epitope within resides 1-22 of SEQ ID NO:1. In certain embodiments, the antibody will specifically bind to an epitope within resides 1-14, 2-14, 2-14, 3-14, 4-14, 5-14, 6-14, 7-14, 8-14, 9-14, 10-14, 14-22 or within residues 23-34 of SEQ ID NO:1, In certain embodiments, the antibody will bind to an epitope present on one of SEQ ID NO:1, 2, 3, 4, 5, 6, 7, 8, 9, 10, 11, 12, 13, 14, 15, 16, 17, 18, 19, 20, 21, or 22. In certain embodiments, the antibody will specifically bind to a region of SEQ ID NOS:1-12 that is outside of the adiponectin binding domain.

The present invention also provides an antibody that specifically binds to an epitope of an adiponectin receptor fragment having SEQ ID NO:23. In certain embodiments, the antibody will specifically bind to a region of SEQ ID NO:23 that is outside of the adiponectin binding domain, i.e., the antibody will specifically bind to an epitope within resides 1-22 of SEQ ID NO:23. In certain embodiments, the antibody will specifically bind to an epitope within resides 1-14, 2-14, 2-14, 3-14, 4-14, 5-14, 6-14, 7-14, 8-14, 9-14, 10-14, 14-22 or within 23-34 residues of SEQ ID NO:23, In certain embodiments, the antibody will bind to an epitope present on one of SEQ ID NO: 23, 24, 25, 26, 27, 28, 29, 30, 31, 32, 33, 34, 35, 36, 37, 38, 39, 40, 41, 42, 43, or 44. In certain embodiments, the antibody will specifically bind to a region of SEQ ID NOS: 23-44 that is outside of the adiponectin binding domain.

V. Correlation of Adiponectin Receptor Fragments with Disease States

For certain of the methods described herein, the level of at least one soluble adiponectin receptor fragment is determined in different patient samples for which either diagnosis or prognosis information is desired, to provide profiles. A profile of a particular sample is essentially a "fingerprint" of the state of the sample. A normal state can be distinguished from a disease state, and within disease states, different prognosis states (good or poor long term survival prospects, for example) can be determined. Diagnosis can be done or confirmed by comparing patient samples with the known profiles. By assessing the evolution of soluble adiponectin receptor fragments different times during disease progression, the stage of disease can be determined as well as the likely prognosis.

A principle of diagnostic testing is the correlation of the results of a procedure with particular clinical parameters. The correlation necessarily involves a comparison between two or more groups distinguished by the clinical parameter. A clinical parameter could be, for example, presence or absence of disease, risk of disease, stage of disease, severity of disease, class of disease or response to treatment of disease. Accordingly, the diagnostician uses this correlation to qualify the status of a subject with respect to the clinical parameter. That is, the diagnostician uses the results of a procedure on a subject to classify or diagnose a subject status with respect to a clinical parameter, the confidence of the diagnosis/classification being related to the classifying or splitting power of the signs or symptoms used in the test.

The methods described herein for qualifying or quantifying soluble adiponectin receptor fragments provide information which can be correlated with pathological conditions, predisposition to disease, therapeutic monitoring, risk stratification, among others.

The present methods are particularly useful for diagnosing conditions, evaluating whether certain drugs will have a desired effect, and determining prognoses. The present methods can be used for early detection of diseases as well as for the optimization of treatment protocols. Preferably the condition, i.e., disease state, will be one associated with abnormal fragmentation patterns of an adiponectin receptor.

For use herein, "diagnosing a condition" refers to determining whether or not a subject has an increased likelihood of having a specified condition. Tests that are used to diagnose a condition, such as the assays described herein, in certain instances, may not be able to diagnose a condition on their own but are used in combination with other tests to diagnose a condition. Accordingly "diagnosing a condition" is meant to include any methods that also aids in the diagnosis of a condition.

In certain embodiments, the invention provides methods for monitoring the progression of disease states in a patient. The method typically comprise the steps of providing a first biological sample from the patient, preferably a urine, blood plasma, blood serum and/or whole blood sample, measuring at least one soluble adiponectin receptor fragment in a first biological sample at a first time point, providing a second biological sample from the patient, measuring the soluble receptor fragment in the second biological sample at a second time point, and determining progression of the disease state in the patient based upon the change in amount of adiponectin receptor fragment or based upon a comparison to measurements from a control population. By measuring the soluble receptor fragments in a patient sample over time, a clinician will be able to determine whether the disease state has worsened or improved. A clinician can therefore utilize these measurements for tailoring treatment appropriately. Methods for monitoring the progression of disease states comprising determining level of at least one soluble C terminal fragment can be combined with other tests to monitor progression of the disease state.

The present inventors have discovered that subjects having an adipocyte imbalance have different patterns of adiponectin receptor fragments in blood than do normal subjects. The present invention thus provides methods of determining whether a subject has an adipocyte imbalance by determining the levels of at least one adiponectin receptor fragment in a bodily fluid sample from the subject.

For example, in order to determine whether a subject has an adipocyte imbalance, once could determine the levels of the fragment described herein. In certain embodiments, the absence or presence of only very low levels of certain fragments, i.e., fragments that are 25 to 34 amino acid in length (i.e., SEQ ID NOS: 1, 2, 4-11, 23, 24, and 26-33) and generally unbound will be indicative of an increased likelihood of having adipocyte imbalance. Conversely, the presence of normal levels of these fragments will be indicative of a normal adipocyte balance. In certain embodiments, the presence of increased amounts of certain smaller fragments, i.e., unbound fragments that are 13 to 24 amino acids in length (i.e., SEQ ID NOS: 3, 12-22, 25, and 34-44) will be indicative of an increased likelihood of having adipocyte imbalance. Conversely, the presence of normal levels of these fragments will be indicative of a normal adipocyte balance. The presence of increased total levels of adiponectin receptor fragments, i.e., total concentration of adiponectin receptor fragments, will be indicative of a respective likelihood of having adipocyte imbalance.

As blood levels of adiponectin decrease, the percentage of patients with disease increases. In patients with blood levels of adiponectin of less than about 4.0 μg/mL, the number of patients diagnosed with metabolic syndrome increases strikingly and the risk for coronary artery disease increases as well. For example, a subject having blood levels of adiponectin of less than or equal to about 4.0 μg/mL has an increased chance of having coronary artery disease as compared to a subject having blood levels of adiponectin of greater than 4.0 μg/mL (odds ratio is greater than 3.0 for men and women or greater than 1.7 in men and greater than 10 in women) The term adiponectin refers to total adiponectin measured including monomers of full length, globular and non-globular portions as was as oligmers of adiponectin. Thresholds can be adjusted for specific assays able to measure individual forms.

By measuring the levels of these fragments in a biological fluid sample obtained from a subject at different time points, it can be determined whether the adipocyte imbalance is improving or worsening. Similarly, by measuring the levels of these fragments before and after therapeutic intervention, it can be determined whether the therapy is effective.

Adiponectin is an adipocyte implicated in a number of disease states, including, for example, obesity, insulin resistance, type II diabetes, metabolic syndrome, dyslipidemia, cardiovascular disease, and hypertension. For use herein, a subject that has hypoadiponectinemia has reduced plasma adiponectin concentrations as compared to normal subjects. Subjects having hypoadiponectinemia can be identified using the present methods.

The present methods can be used to determine onset of hypoadiponectinemia, progression of hypoadiponectinemia, and/or efficacy of treatment of hypoadiponectinemia in a subject. Similarly, the present methods can be used to determine onset of a condition characterized by hypoadiponectinemia, progression of a condition characterized by hypoadiponectinemia, and/or efficacy of treatment of a condition characterized by hypoadiponectinemia in a subject.

For example, in order to determine whether a subject has hypoadiponectinemia, one can determine the levels of the fragment described herein. In certain embodiments, the absence or presence of increased levels of certain fragments, i.e., generally unbound fragments that are about 13 to 24 amino acids in length (i.e., SEQ ID NOS: 3, 12-22, 25, and/or 34-44) will be indicative of an increased likelihood of having hypoadiponectinemia. In certain embodiments, the presence of decreased amounts of certain larger fragments, i.e., generally unbound fragments that are 25 to 34 amino acids in length (i.e., SEQ ID NOS: ID NOS: 1, 2, 4-11, 23, 24, and/or 26-33) will be indicative of an increased likelihood of having hypoadiponectinemia. The presence of increased levels of total adiponectin receptor fragments, unbound or bound to carrier protein, i.e., adiponectin, will generally be indicative of a respective likelihood of having hypoadiponectinemia.

By measuring the levels of these fragments in a biological fluid sample taken from a subject at different time points, it can be determined whether the hypoadiponectinemia is improving or worsening. Similarly, by measuring the levels of these fragments before and after therapeutic intervention, it can be determined whether the therapy is effective.

Normal insulin sensitivity results when insulin causes fat cell to produce adiponectin. Full length adiponectin aggregates into multimers, typically called LMW, MMW and HMW forms. Adiponetin interacts with the adiponectin receptor 2 in the liver and adiponectin receptor 1 in the muscle to stop glucose production and cause glycolysis and fatty acid oxidation. The adiponectin receptor 1 reacts with a cleaved form of adiponectin called globular adiponectin where as adiponectin receptor 2 reacts to full length adiponectin. Globular adiponectin was recently shown by others to form by action of blood elastase.

Insulin resistance occurs when adipocytes become hypertropic and produce less adiponectin in response to insulin. In this state, the cells become more apoptotic and cell division slows. As a result plasma adiponectin levels decreases. Insulin levels rise in an effort to cause cells to release more adiponectin. However as the insulin resistance worsens more insulin and less adiponectin is produced. The lesser adiponectin results in less glycolysis and fatty acid oxidation in muscle and prevents liver glucose production from stopping.

For use herein, insulin resistance refers to a decrease in an individual in the biological action of insulin in vivo as assessed by the rate of disposal of glucose from the bloodstream (e.g., into insulin-sensitive tissue, such as muscle, fat and liver).

Diabetes mellitus is defined as chronic hyperglycemia due to defective insulin secretion and/or action. The two major classifications of the disease are type I, which involves pancreatic beta-cell destruction, usually by an autoimmune process, and type II, impaired physiological effectiveness of insulin, i.e., insulin resistance. Diabetes mellitus is often first diagnosed by the demonstration of hyperglycemia through the use of random or fasting plasma glucose determinations, or by an oral glucose tolerance test. Glucose tolerance tests do not measure insulin resistance.

Once diabetes is diagnosed, assays for insulin and C-peptide can be used to differentiate between type I and type II diabetes, and among type II diabetes, to distinguish those who require insulin treatment from those who can be managed with changes in diet and exercise patterns. It is difficult to distinguish those needing insulin treatment from borderline cases who can be managed with changes in diet and exercise alone.

Insulin is a polypeptide hormone released by pancreatic beta cells to reduce blood glucose levels by promoting cellular uptake of glucose and suppressing endogenous glucose. The immediate precursor of insulin is proinsulin (MW, 9 kDa), a single-chain polypeptide consisting of 86 amino acids with three disulfide bridges. Proteolytic cleavage produces insulin (MW, 6 kDa) which consists of 51 amino acids in two chains joined by two disulfide bridges; and the connecting peptide (C-peptide; MW, 3 kDa), a single polypeptide chain containing 31 amino acids. Equimolar amounts of insulin and C-peptide are then secreted into circulation. Circulating C-peptide concentrations are approximately 5- to 10-fold higher than those of insulin as a result of the much longer half-life of C-peptide. C-peptide is therefore a measure of the body's natural insulin production and can be measured in the presence of intravenous synthetic insulin.

The gold standard for measurement of insulin resistance is the glucose clamp method (M value) to measure glucose infusion rate (GIR) adjusted by insulin infusion rate (IIR) to maintain a blood glucose level. A second common measurement is the fasting glucose and insulin (HOMA-IR). It has been reported that M value (as determined by glucose clamp method, a gold standard) correlated with blood levels of adiponectin show that adiponectin can be an indicator for insulin resistance. An additional correlation is the measurement of the fasting glucose and insulin blood levels corrected by adiponectin (FBS×FIRI/AND) (fasting blood glucose×fasting insulin level/adiponectin).

The present methods can be use to identify subjects having insulin resistance. Further, the present methods can be used to determine the severity of insulin resistance in diabetic subjects and to recommend the appropriate treatment.

For example, in order to determine whether a subject has insulin resistance, one can determine the levels of the fragment described herein. In certain embodiments, the absence or presence of decreased levels of certain fragments, i.e., fragments that are 25 to 34 amino acid in length, and that are generally unbound, (i.e., SEQ ID NOS: 1, 2, 4-11, 23, 24, and/or 26-33) will be indicative of an increased likelihood of having insulin resistance. Conversely, the presence of normal levels of these fragments will be indicative of a normal state. In certain embodiments, the presence of increased levels of certain smaller fragments, i.e., unbound fragments that are 13 to 24 amino acids in length (i.e., SEQ ID NOS: 3, 12-22, 25, and/or 34-44) will be indicative of an increased likelihood of having insulin resistance. Conversely, the presence of normal levels of these fragments will be indicative of a normal state. An increase in total concentration of adiponectin receptors fragments (bound or unbound) to carrier protein, i.e., adiponectin, is generally indicative of an increased likelihood of having insulin resistance.

By measuring the levels of these fragments in a biological fluid sample taken from a subject at different time points, it can be determined whether the insulin resistance is improving or worsening. Similarly, by measuring the levels of these fragments before and after therapeutic intervention, it can be determined whether the therapy is effective.

Metabolic syndrome has been associated with reduced plasma adiponectin levels and can be monitored using the methods of the present invention. Metabolic syndrome, also known as syndrome X, is a cluster of risk factors that is blamed for the excess cardiovascular disease morbidity among overweight and obese patients and patients with type 2 diabetes mellitus.

Both the World Health Organization and National Cholesterol Education Program—Adult Treatment Patent (NCEP-ATP III) have set forth diagnostic criteria for metabolic syndrome. For use in the present invention, metabolic syndrome is defined by the WHO diagnostic criteria as provided below (Darwin Deen, American Family Physician, 69(12) (2004) 2875-2882).

TABLE 1

Diagnostic Criteria for Metabolic Syndrome According to the WHO

| Component | WHO diagnostic criteria (insulin resistance* plus two of the following) |
|---|---|
| Abdominal/central obesity | Waist to hip ratio: >0.90 (men), >0.85 (women), or BMI >30 kg per m$^2$ |
| Hypertriglyceridemia | ≥150 mg per dL (≥1.7 mmol per L) |
| Low HDL cholesterol | <35 mg per dL (<0.9 mmol per L) for men, <39 mg per dL (<1.0 mmol per L) for women |

TABLE 1-continued

Diagnostic Criteria for Metabolic Syndrome According to the WHO

| Component | WHO diagnostic criteria (insulin resistance* plus two of the following) |
|---|---|
| High blood pressure | ≥140/90 mm Hg or documented use of antihypertensive therapy |
| High fasting glucose | Impaired glucose tolerance, impaired fasting glucose, insulin resistance, or diabetes |
| Microalbuminuria | Urinary albumin to creatinine ratio: 30 mg per g, or albumin excretion rate: 20 mcg per minute |

WHO = World Health Organization; ATP = Adult Treatment Panel; BMI = body mass index; HDL = high-density lipoprotein.
*Insulin resistance is identified by type 2 diabetes mellitus or impaired fasting glucose.

The present inventors have found that the level of soluble adiponectin receptor fragments in bodily fluid is an indicator of metabolic syndrome in a subject. Accordingly, the present method can be use to identify subjects having metabolic syndrome. These methods can be used in combination with any one of the other diagnostic criteria for identifying metabolic syndrome.

For example, in order to determine whether a subject has metabolic syndrome, one can determine the levels of the fragment described herein. In certain embodiments, the absence or presence of decreased levels of certain fragments, i.e., fragments that are 25 to 34 amino acid in length (i.e., SEQ ID NOS: 1, 2, 4-11, 23, 24, and/or 26-33), and that are generally unbound will be indicative of an increased likelihood of having metabolic syndrome. Conversely, the presence of normal levels of these fragments will be indicative of a normal state. In certain embodiments, the presence of increased amounts of certain smaller fragments, i.e., fragments that are 13 to 24 amino acids in length (i.e., SEQ ID NOS: 3, 12-22, 25, and/or 34-44) will be indicative of an increased likelihood of having metabolic syndrome. An increase in total concentration of adiponectin receptor fragments, unbound or bound to carrier protein, i.e., adiponectin, is generally indicative of an increased likelihood of having metabolic syndrome.

Acute Coronary Syndromes (ACS) has been applied to a group of coronary disorders that result from ischemic insult to the heart. Acute coronary syndrome is defined as a vascular blockage of greater than 60% by angiograph evaluation with our without a cardiac condition.

The present inventors have found that the level of soluble adiponectin receptor fragments in bodily fluid is an indicator of vascular blockage in a subject. Accordingly, the present method can be use to identify subjects having a vascular blockage. These methods can be used in combination with any one of the other diagnostic criteria for identifying vascular blockages.

For example, in order to determine whether a subject has a vascular blockage, one can determine the levels of the fragment described herein. In certain embodiments, the absence or presence of decreased levels of certain fragments, i.e., fragments that are 25 to 34 amino acid in length (i.e., SEQ ID NOS: 1, 2, 4-11, 23, 24 and/or 26-33), and that are generally unbound will be indicative of an increased likelihood of having vascular blockage. Conversely, the presence of normal levels of these fragments will be indicative of a normal state. In certain embodiments, the presence of increased amounts of certain smaller fragments, i.e., fragments that are 13 to 24 amino acids in length (i.e., SEQ ID NOS: 3, 12-22, 25, and/or 34-44) will be indicative of an increased likelihood of having vascular blockage. Conversely, the presence of normal levels of these fragments will be indicative of a normal state. An increase in total concentration of adiponectin receptor fragments unbound or bound to carrier protein, i.e., adiponectin, is generally indicative of an increased likelihood of having a vascular blockage.

A cardiac condition, also known as a cardiovascular disease condition, generally means disease which results from a cardiovascular insufficiency, including, but not limited to, coronary heart disease (which further includes myocardial infarction and angina pectoris) or coronary artery disease, stroke, congenital heart failure and congestive heart failure, congenital heart failure, and high blood pressure. Coronary heart disease also includes myocardial infarction and angina pectoris. Cardiovascular diseases are generally characterized by an impaired supply of blood to the heart or other target organs. "Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

Coronary heart disease (CHD) is caused by a thickening of the inside walls of the coronary arteries. This thickening, called atherosclerosis, narrows the space through which blood can flow, decreasing and sometimes completely cutting off the supply of oxygen and nutrients to the heart. Atherosclerosis usually occurs when a person has high levels of cholesterol in the blood. Cholesterol and fat, circulating in the blood, build up on the walls of the arteries. The buildup narrows the arteries and can slow or block the flow of blood. When the level of cholesterol in the blood is high, there is a greater chance that it will be deposited onto the artery walls. This process begins in most people during childhood and the teenage years, and worsens as they get older.

Congestive heart failure or (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

Myocardial infarction generally results from atherosclerosis of the coronary arteries, often with superimposed coronary thrombosis. It may be divided into two major types: transmural infarcts, in which myocardial necrosis involves the full thickness of the ventricular wall, and subendocardial (non-transmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

Angina pectoris ("angina") is a recurring pain or discomfort in the chest that happens when some part of the heart does not receive enough blood. It is a common symptom of coronary heart disease (CHD), which occurs when vessels that carry blood to the heart become narrowed and blocked due to atherosclerosis.

The diagnosis and monitoring of all of these diseases by the present methods is encompassed by the present invention.

For example, the present inventors have found that the level of soluble adiponectin receptor fragments in bodily fluid is an indicator of whether a subject, particularly a subject already suffering from arteriosclerosis, is likely to develop or have congestive heart failure, myocardial infarction, or ischemia. Accordingly, the present method can be use to identify subjects having congestive heart failure, myocardial infarction, or ischemia. These methods can be used in combination with any one of the other diagnostic criteria for identifying these conditions.

For example, in order to determine whether a subject has or is likely to develop congestive heart failure, myocardial infarction, or ischemia, one can determine the levels of the fragments described herein. In certain embodiments, the absence or presence of decreased levels of certain fragments, i.e., fragments that are 25 to 34 amino acid in length (i.e., SEQ ID NOS: 1, 2, 4-11, 23, 24, and/or 26-33), and that are generally unbound will be indicative of an increased likelihood of having congestive heart failure, myocardial infarction, or ischemia. Conversely, the presence of normal levels of these fragments will be indicative of a normal state. In certain embodiments, the presence of increased amounts of certain smaller fragments, i.e., unbound fragments that are 13 to 24 amino acids in length (i.e., SEQ ID NOS: 3, 12-22, 25, and/or 34-44) will be indicative of an increased likelihood of having congestive heart failure, myocardial infarction, or ischemia. Conversely, the presence of normal levels of these fragments will be indicative of a normal state. An increase in total concentration of adiponectin receptor fragments unbound or bound to carrier protein, i.e., adiponectin, is generally indicative of an increased likelihood of having congestive heart failure, myocardial infarction, or ischemia.

Similarly, the present methods can be used to identify subjects having hypertension, obesity, lipidemia, or inflammation. These methods can be used in combination with any one of the other diagnostic criteria for identifying these conditions. In all of these conditions, in certain embodiments, the absence or presence of decreased levels of certain fragments, i.e., fragments that are 25 to 34 amino acid in length (i.e., SEQ ID NOS: SEQ ID NOS: 1, 2, 4-11, 23, 24, and/or 26-33), and that are generally unbound will be indicative of an increased likelihood of having the condition. Conversely, the presence of normal levels of these fragments will be indicative of a normal state. In certain embodiments, the presence of increased amounts of certain smaller fragments, i.e., unbound fragments that are 13 to 24 amino acids in length (i.e., SEQ ID NOS: 3, 12-22, 24, and/or 34-44) will be indicative of having the condition. Conversely, the presence of normal levels of these fragments will be indicative of a normal state. An increase in total concentration of adiponectin receptor fragments unbound or bound to carrier protein, i.e., adiponectin, is generally indicative of an increased likelihood of having the condition.

The present invention provides diagnostic, prognostic and therapeutic methods using the specific measurement of at least one fragment described herein. The methods involve first providing a measurement of the adiponectin receptor fragment and then correlating the measurement with a disease state. By correlating the measurement, one is able to qualify the subject status with respect to the particular clinical parameter in question. In a preferred embodiment, the measurement is made by affinity mass spectrometry as discussed above.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives that test as positive. Negative predictive value is the percentage of actual negatives that test as negative.

The fragments described herein, individually, or, in combination, are useful in aiding in the determination of a disease status. In certain embodiments, first, the selected biomarker, i.e., particular fragment, is measured in a subject sample using the methods described herein, e.g., capture on a SELDI biochip followed by detection by mass spectrometry. Then, the measurement is compared with a diagnostic amount or cutoff that distinguishes one diagnostic parameter from another, e.g., a positive insulin resistance parameter from a negative insulin resistance parameter. The diagnostic amount represents a measured amount of a biomarker above which or below which a subject is classified as having a particular disease. For example, if the fragment is up-regulated compared to normal in the disease state, then a measured amount above the diagnostic cutoff provides a diagnosis of disease. Alternatively, if the biomarker is down-regulated in the disease, then a measured amount below the diagnostic cutoff provides a diagnosis of the disease. As is well understood in the art, by adjusting the particular diagnostic cutoff used in an assay one can increase sensitivity or specificity of the diagnostic assay depending on the preference of the diagnostician.

In some embodiments, the mere presence or absence of a particular fragment, without quantifying the amount of the fragment, is useful and can be correlated with a probable diagnosis of, disease, i.e., insulin resistance. Thus, a detected presence or absence, respectively, of these markers in a subject can indicate that the subject has a higher probability of having insulin resistance.

In certain embodiments of the methods of qualifying disease status, the methods further comprise managing subject treatment based on the status. Such management describes the actions of the physician or clinician subsequent to determining disease status. For example, if a physician makes a diagnosis of disease, then a certain treatment regimen will be followed. For example, for many people, cardiovascular heart disease is managed with lifestyle changes and medications. Others with severe cardiovascular heart disease may need surgery. In any case, once cardiovascular heart disease develops, it requires lifelong management. Alternatively, a diagnosis of no coronary heart disease status or other cardiovascular disease status might be followed with no treatment. If the diagnostic test gives an inconclusive result on concerning coronary heart disease status, further tests may be called for.

While individual biomarkers are useful diagnostic markers, it has been found that a combination of biomarkers can provide greater predictive value of a particular status than single markers alone. Specifically, the detection of a plurality of markers in a sample can increase the percentage of true positive and true negative diagnoses and decreases the percentage of false positive or false negative diagnoses. Accordingly, in certain embodiments, the present methods involve detecting a plurality of the fragments described herein.

Accordingly, in one aspect, this invention provides a method for discovering patterns of adiponectin receptor fragments, which patterns correlate with a clinical parameter of interest.

In certain embodiments, the present invention provides methods for measuring the response to therapy comprising the steps of providing a first biological sample, preferably a urine and/or blood plasma sample, measuring the amount of at least one soluble adiponectin receptor fragment in the first biological sample at a first time point, providing a second biological sample from the patient, measuring the fragment in the second biological sample at a second time point, and determining response in the patient based upon the change in the amount of the fragment or based upon a comparison to a control population. The subject may be a positive responder, poor responder, or non-responder. For use herein, a positive responder, is a subject who positively responds to treatment, i.e., a subject who experiences success in amelioration of the condition, including any objective or subjective parameter such as abatement; remission; diminishing of symptoms or making the condition more tolerable to the patient; slowing in the rate of degeneration or decline; making the final point of degeneration less debilitating; or improving a subject's physical or mental well-being. A positive responder is one in which any toxic or detrimental side effects of the biologically active agent is outweighed in clinical terms by therapeutically beneficial effects. A non-responder is a subject who doesn't respond to the treatment or doesn't respond to a satisfactory level. A poor responder is a subject who responds to treatment but not at the level of the positive responder.

In certain embodiments wherein the disease state is insulin resistance or another condition related to insulin resistance such as diabetes or metabolic syndrome, the therapeutic treatment generally comprises the step of administering an effective amount of one or more insulin sensitizing pharmaceuticals. Insulin sensitizing pharmaceuticals are known in the art and include, for example, PPAR agonists such as a thiazolidinedione (also referred to as a TZD); or PPAR gamma partial agonists, also known as selective PPAR gamma modulators (SPPARM's), PPAR alpha-gamma dual partial agonists (selective PPAR alpha-gamma dual selective modulators)' and PPAR pan-agonists. PPAR gamma agonists that have a TZD structure include pioglitazone, rosiglitazone, ciglitazone, darglitazone, englitazone, balaglitazone, isaglitazone, troglitazone, netoglitazone, MCC-555, and BRL-49653. Other PPAR gamma agonists, some of which have a TZD structure, include CLX-0921, 5-BTZD, GW-0207, LG-100641, LY-300512, NN-2344, LY 818, GW-677954, GW-7282, and T-131. PPAR alpha/gamma dual agonists that exhibit both alpha and gamma agonism and can be used to treat type 2 diabetes and to reduce lipids. PPAR alpha/gamma agonists include KRP-297 (MK-0767), muraglitazar (BMS-298585), farglitazar, ragaglitazar, tesaglitazar (AZ-242), JT-501, GW-2570, GI-262579, CLX-0940, GW-1536, GW1929, GW 2433, L-796449, LR-90, SB-219994, LY-578, LY-4655608, LSN-862, LY-510929, and LY-929.

The methods described herein can be used to determine whether a patient is likely to be a responder to treatment with any drug used to treat type 2 diabetes or insulin resistance including, for example, a biguanide (e.g. metformin); a sulfonylurea; another chemical class of insulin secretagogue other than a sulfonylurea, such as a meglitinide; insulin (which can be formulated for subcutaneous or intramuscular injection, or in a formulation for avoiding the need for injection, such as oral, buccal, or nasal); a DP-IV inhibitor; a PTP-1B inhibitor; a GLP-1 analog; a glycogen phosphorylase inhibitor; a glucagon receptor antagonist; a hydroxysterol dehydrogenase (HSD-1) inhibitor; a glucokinase activator; or a TZD or non-TZD PPAR gamma agonist; or any combination of treatment thereof.

The methods described herein can be used to determine whether a patient is likely to be a responder to treatment with any drug that can be used to treat obesity in an obese patient who also has type 2 diabetes or insulin resistance, including, for example, ibutramine, orlistat, phentermine, an Mc4r I agonist, cannabinoid receptor 1 (CB-1) antagonist/inverse agonist, a 33 adrenergic agonist; or a TZD or non-TZD PPAR gamma agonist; or any combination of treatment thereof.

The methods described herein can be used to determine whether a patient is a responder to treatment with any drug used to reduce total cholesterol or LDL-cholesterol and/or raise HDL-cholesterol, including, for example, an HMG-CoA reductase inhibitor (lovastatin, simvastatin, rosuvastatin, pravastatin, fluvastatin, atorvastatin, rivastatin, pitavastatin, ZD-4522, and other stating); niacin; a cholesterol absorption inhibitor (ezetimibe); a CETP inhibitor (torcetrapib); a PPAR alpha agonist (fenofibrate, gemfibrizol, clofibrate, or bezafibrate); an ACAT inhibitor (avasimibe); an anti-oxidant (probucol); or a bile acid sequestrant (cholestyramine), or a TZD or non-TZD PPAR gamma agonist; or any combination of treatment thereof.

In certain embodiments, the level of adiponectin receptor fragments is determined before treatment begins and then after treatment has proceeded for a time long enough for the changes in the level or patterns of the fragments to reflect whether the patient will respond to treatment. After treatment has proceeded, a patient who is a likely responder to the therapeutic will have increased levels of certain fragments, i.e., fragments that are 25 to 34 amino acid in length (i.e., SEQ ID NOS: 1, 2, 4-11, 23, 24, and/or 26-33) and that are generally unbound, and decreased amounts of certain smaller fragments, i.e., fragments that are 13 to 24 amino acids in length (i.e., SEQ ID NOS: 3, 12-22, 24, and/or 34-44). In certain embodiments, the differences will be observed within four weeks after treatment commences, preferably within two weeks after treatment commences, and most preferably within one week after treatment commences.

VI. Additional Biomarkers

In certain embodiments, assessment of one or more additional markers are combined to increase the predictive value of the analysis in comparison to that obtained from measurement of adiponectin receptor fragments alone. For example one or more markers for the disease state, i.e., adipocyte imbalance, insulin resistance, diabetes, metabolic syndrome, acute coronary syndrome (i.e., vascular blockage), cardiovascular heart disease, stroke, congenital heart failure, congestive heart failure, hypertension, angina, myocardial infarction, ischemia, atherosclerosis, obesity, lipidemia, or inflammation, can be measured along with adiponectin receptor fragments to enhance the predictive value of the described methods. Biomarkers that can be used in combination with the present methods include for example, adipocyte factors, for example, adiponectin, leptin, visfatin, klotho, glucagon-like peptide-1 (GLP-1), DDPIV, resistin, ghrelin, AMP-activated protein kinase (AMPK), Sirt1, PPAR agonists, ARNT (aryl hydrocarbon receptor nuclear translocator), HIF1B, C-peptide, Foxa2, insulin, or glucose, including fragments, peptides and variants thereof and/or inflammation markers, for example, RBF-4, C-reactive protein (CRP), resistin, MCP-1, IL-6, TNF-α, IL-1 beta, PAI-1, bikunin, auto-immune factors, autoantibodies to glutamic acid, Islet cell auto-antibodies, insulin auto-antibodies, autoantibodies to IL-2, autoantibodies to IA-2, incretins, and other auto-immune factors and fragments, peptides or variants thereof.

The methods described herein can be used in combination with any other tests that will aid in the diagnosis of a disease, determination of progression of a disease, or determination of efficacy of treatment of a disease.

In certain embodiments, adiponectin levels will also be measured in the subject. Methods of measuring adiponectin and correlating adiponectin levels with disease states are known in the art, see for example, U.S. Pat. No. 6,461,821, U.S. Publication Nos. Us20050054005 and US20050048565, and International Publication Numbers WO2004086040, WO2005046734, WO2005038457, and WO2004022596, each of which is incorporated herein by reference in its entirety and for all purposes. For use herein, the term adiponectin includes variants thereof having adiponectin activity. In certain embodiments, the amount of total adiponectin, the amount of low molecular weight, the amount of high molecular weight adiponectin or the ratio between these numbers will be used in combination with the methods of the present invention. Accordingly, the present methods can include the step of measuring the level of adiponectin (total adiponectin, high molecular weight adiponectin, low molecular weight adiponectin, or other forms of adiponectin, including fragments and variants thereof) in a biological sample from a subject and correlating the amount with the presence of a disease state, with progression of disease, or efficacy of treatment. Reduced amounts of adiponectin are indicative of a disease as well as a smaller ratio of high molecular weight adiponectin to total or low molecular weight adiponectin.

In certain embodiments, leptin levels will be measured in the subject. Methods of measuring leptin, including variants thereof, and correlating leptin levels with disease states are known in the art. (See, for example, Gorden and Gavrilova, Current Opinon in Pharmacology, (2003) 3:655-659, incorporated herein by reference in its entirety and for all purposes).

In certain embodiments, brain natriuretic peptide (BNP) levels can be measured to aid in the diagnosis or progression of vascular blockage and cardiovascular disease. Methods of measuring BNP levels and correlating them with disease states are known in the art. See, for example, Frank Peacock, Cleveland Clinic Journal of Medicine (2002), 69(3) 243-251, incorporated herein by reference in its entirety and for all purposes.

The present methods can be used to identify subjects having inflammation and certain diseases characterized by excessive inflammation. These methods can be used in combination with known methods of determining levels of inflammation in a subject.

In certain embodiments, bikunin and/or uristatin levels will be measured in the subject. Bikunin represents the inhibitory light chain of the inter-α-trypsin inhibitor protein. It is a protease inhibitor, known to be elevated in the urine of patients with inflammatory diseases and is considered an acute phase protein. For use herein the term bikunin includes variants thereof having bikunin activity. Uristatin is a trypsin inhibitor present in urine that is increased in most patients with bacterial or viral infections and in many with inflammatory disorders. Methods of measuring bikunin or uristatin, including variants thereof, and correlating bikunin or uristatin levels with disease states are known in the art. Uristatin is a trypsin inhibitor present in urine that is increased in most patients with bacterial or viral infections and in many with inflammatory disorders. (Pugia and Lott, Clin. Chem Lab Med 2005 43(1):1-16, International Publication No. WO200504022, each of which incorporated herein by reference in its entirety and for all purposes).

In certain embodiments, C-reactive protein levels will be measured in the subject. Methods of measuring C-reactive protein, including variants thereof, and correlating C-reactive protein levels with disease states are known in the art. For example C-reactive protein in present in the blood serum during episodes of acute inflammation or infection. CRP levels of about 1 mg/dL is usually considered high for CRP and most infections and inflammations result in CRP levels above 10 mg/dL. For use herein the term C-reactive protein includes variants thereof having C-reactive protein activity. (Pugia and Lott, Clin. Chem Lab Med 2005 43(1):1-16, incorporated herein by reference in its entirety and for all purposes).

In certain embodiments, a white blood cell count can be performed in combination with the methods described herein. Methods of measuring white blood cells and correlating white blood cell levels with disease states are known in the art. White blood cell (WBC) count, or the measure of white blood cells in the blood, is a reliable and widely used marker that reflects inflammation throughout the body. WBC count is also linked to other chronic conditions, including cardiovascular disease, hypertension and diabetes.

In certain embodiments, fasting glucose, glucose tolerance measurements, and/or insulin and glucagon-stimulated C-peptide levels will be measured in the subject. Methods of measuring insulin and C-peptide, including variants thereof, and correlating insulin and C-peptide levels with disease states are known in the art. For example, glucagon-stimulated C-peptide levels greater than about 1.8 ng/mL have been reported to identify type 2 diabetics who could be managed without insulin treatment. Typically, 3.0 ng/mL is used as an upper limit indicative of hyperinsulinemia or insulin resistance. In contrast, levels less than about 0.5 ng/mL reportedly identify type 1 patients requiring insulin treatment due to hypoinsulinemia. The normal reference range for normal adults is 0.5-2 ng/mL.

In embodiments wherein one or more markers are used in combination with adiponectin receptor fragments to increase the predictive value of the analysis, the level of the additional markers can be measured in the same biological sample from the subject or in another, which can be of the same type or of a different type. For example, the level of adiponectin receptor fragments can be measured in a sample of blood plasma, while the level of an additional marker, can be measured in the same sample of plasma, a different sample of plasma, or in a sample of serum or urine from the subject.

VII. Additional Disease States

Adiponectin is involved in many process and pathways in the body. Accordingly, the detection of the fragmentation pattern of adiponectin receptor fragments can be used to determine the onset, monitor progression and/or determine the efficacy of drug treatment for many disease states. In particular, the detection of soluble adiponectin receptor fragments can be used in combination with other diagnostic methods and tools for determining the onset, monitoring progression and/or determining the efficacy of drug treatment for many disease states. In particular, the detection of soluble adiponectin receptor fragments can be associated with angiogenic, atherogenic, and macrophages transformation of cells. Adiponectin receptor 1 is upregulated by binding to LXR nuclear receptors which are activated by fatty acids and LXR receptors are integral to macrophage transformation. Adiponectin receptor 1 expression has also shown to be increased during monocyte transformation.

Accordingly, inflammatory diseases, i.e., disease triggered by cellular or non-cellular mediators of the immune system or tissues causing the inflammation of body tissues and subsequently producing an acute or chronic inflammatory condition, can be detected and monitored using the present methods. Examples of such disease, include, for example, hypersensitivity of type I-IV, for example, hypersensitivity disease of the lung including asthma, atopic diseases, allegic rhinitis or conjunctivitis, angioedema of the lids, hereditary agioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, rheumatoid arthritis, psoriasis, Crohn's disease, scleroderma, mixed connective tissue disease, polymyositis, sarcoidosis, urinary tract infection, IgA nephropathy, glomerulonephritis, acute or chronic host graft reactions.

Cancers can also be detected and monitored using the present methods. Cancer refers to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. The term cancer includes, but is not limited to, cancers of the female reproductive organs including, but not limited to, ovarian cancer, cervical cancer and uterine cancer; lung cancer; breast cancer; renal cell carcinoma; Hodgkin's lymphoma; Non-Hodgkin's lymphoma; cancers of the genitourinary system including, but not limited to, kidney cancer, prostate cancer, bladder cancer, and urethral cancer; cancers of the head and neck; liver cancer; cancers of the gastrointestinal system including, but not limited to, stomach cancer, esophageal cancer, small bowel cancer or colon cancer; cancers of the biliary tree; pancreatic cancer; cancers of the male reproductive system including, but not limited to, testicular cancer; Gestational trophoblastic disease; cancers of the endocrine system including, but not limited to, thyroid cancer, parathyroid cancer, adrenal gland cancer, carcinoid tumors, insulinomas and PNET tumors; sarcomas, including but not limited to, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, but not limited to all forms of leukemia, myelodysplastic syndromes, myeloproliferative disorders and multiple myeloma.

VIII. Kits

For use in the applications described or suggested above, kits are also provided by the invention. Such kits can, for example, comprise a carrier means being compartmentalized to receive in close confinement one or more container means such as strips, cassettes, microfluidic chips, vials, tubes, and the like, each of the container means comprising one of the separate elements to be used in the method. For example, one of the container means can comprise a probe that is or can be detectably labeled. Such probe can be an antibody or polynucleotide specific for a soluble C-terminal receptor fragment.

In addition, the kits can include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips, and the like), optical media (e.g., CD ROM), and the like. Such media can include addresses to internet sites that provide such instructional materials.

The kit can also comprise, for example, a means for obtaining a biological sample from an individual. Means for obtaining biological samples from individuals are well known in the art, e.g., catheters, syringes, and the like, and are not discussed herein in detail.

The following Exemplary Embodiments of specific aspects for carrying out the present invention are offered for illustrative purposes only, and are not intended to limit the scope of the present invention in any way.

EXAMPLES

Example 1

Detection of C-Terminal Fragments in Diabetic Individuals

One hundred and sixteen patients were assessed by medical history. Fifty had no history of diabetes or metabolic risk factors (lipids, hypertension, obesity) were not diagnosed as metabolic syndrome according to WHO definition. Sixty nine had a history of diabetes either Type 1 or Type2. Insulin resistance was further assessed in all patients by glucose measurement, c-peptide and hemoglobin A1c.

Adiponectin, c-peptide, insulin. and HMW Adiponectin were measured using commercial ELISA kit. HbA1c was measured with the DCA 2000+ instrument (Bayer) and glucose by the YSI. The following AdipoR1 ELISA assay was used to measure all C-terminal fragments whether bound or unbound.

The materials for the ELISA assay of C-terminal fragment AdipoR1 included microtiter plates (Costar PN 3690, high binding;), Tris Buffered Saline (TBS) (Pierce Product Number 28376), Adiponectin receptor 1 (AdipoR1) peptide (peptides 16-34) (Phoenix Pharmaceuticals, Inc., Product Number 001-44), Super Block in TBS (Pierce Product Number 37535), TBS/TW—Tris Buffered Saline containing 0.05% Tween 20 (Tween 20—Pierce Product Number—P8341), Rabbit anti-AdipoR1 antibody (Phoenix Pharmaceuticals, Inc., Product Number G-001-44), ALP-Goat anti-rabbit IgG (Sigma Product Number A 3687), 1-Step PNPP (Pierce Product Number 37621) and 2N NaOH.

Reagents were prepared as follows. A stock solution of AdipoR1 peptide (Phoenix Pharmaceuticals, Inc., Product Number 001-44) was prepared by dissolved 100 ug peptide in 100 uL 60% Acetonitrile containing 0.1% TFA as directed. This was further diluted this 1.0 mg/mL solution to 10 mL with nanopure water aming aa 10 ug/mL stock solution. This solution was aliquoted 500 uL per vial is being stored frozen at −70° C. A 0.10 ug/mL AdipoR1 peptide in TBS was used to coat plates and was prepared by adding 100 uL of 10 ug/mL AdipoR1 peptide in TBS (A above) to 9900 uL of TBS and mixing well. A stock solution of Rabbit anti-AdipoR1 (Phoenix Pharmaceuticals, Inc., Product Number G-001-44) was prepared by dissolved 200 uG antibody in 200 uL nanopure water as directed. This makes a 1.0 mg/mL antibody solution. Aliquot into 50 uL aliqouts and store frozen at −70° C. A solution of 6.0 ug/mL Rabbit anti-AdipoR1 in Super Blocker made by adding 18.0 uL of stock anti-AdipoR1 into 2982 uL of Super Blocker and mix well. A solution of 3.75 ug/mL Rabbit anti-AdipoR1 in Super Blocker (used to dilute plasma samples 5-fold; change concentration for other dilutions) was made by adding 56.25 uL of stock anti-AdipoR1 (C) to 15,000 uL of Super Blocker and mixing well. A 1/2000 dilution of ALP-Goat anti-rabbit IgG was made by adding 7.5 uL ALP-Goat anti-rabbit IgG (Sigma, Product Number A 3687) into 15.0 mL Superblocker and mixing well.

Preparation of calibrators were done using AdipoR1 peptide in superblocker containing 3.0 ug/mL Rabbit anti-AdipoR1 to achieve AdipoR1 peptide concentrations of 5.0, 2.5, 1.25, 6.25, 0.312, 0.156, 0.078 and 0 ug/mL The method for AdipoR1 ELISA Assay was done by coating the micortiter plate with 50 uL/well of 0.10 ug/mL AdipoR1 peptide in TBS, and store at 4° C. for minimum of 72 hours, removing the coated microtiter plate from the refrigerator, and emptying the plate and wash the 3 times with 200 uL/well TBS. This was followed by adding 150 uL of Super Block buffer (Pierce PN 37535) to each well and shaking the plate for 30 min at 25° C. The plate was emptied and wash 5 times with TBS/TW. This is followed by the addition of the prepared calibrators containing 5000, 2500, 1250, 625, 312, 156, 78, and 0 ng/mL AdipoR1 peptide or of samples diluted 5-fold with blocker buffer. All samples and calibators contained 3.0 ug/mL Rabbit anti-AdipoR1. The samples or calibrates were added as 50 uL/well and incubated overnight at 5° C. in a refrigerator. This was followed by emptying the plate and wash 5 times with TBS/TW.

The 1/2000 dilution of ALP-Goat anti-rabbit IgG in Super Blocker was added at 50 uL/well to all the wells in the ELISA Template. This was incubated for 2 hours at 25° C. on the Jitterbug Shaker at shaker setting #2. The plate was empties and wash the 5 times with TBS/TW. 50 uL of 1-Step PNPP (Pierce PN 37621) was added to each well. The plate was incubated for 30 min at 25° C. on the Jitterbug Shaker. 25 uL of 2N NaOH was added to each well to stop the enzyme reaction. The plate was allowed to stand at least 5 min before reading at 405 nm. A fit calibrator data to a standard curve and calculate unknowns. (Single phase exponential decay usually gives best fit.) was done to calculate the values in the sample.

Adiponectin decreases with type 2 diabetes. Adiponectin was unchanged with type 1 diabetes. Adiponectin was higher in normal controls and Type 1 patients compared to Type 2 (see Table 2). Adiponectin decreased and then increased with HbA1c. All differences are small and not very significant with T-values below 1.4 (Probability of <80% significance). Adiponectin differences were not predictive of BMI (body mass index).

Use of a ratio of HMW Adiponectin/total improves differences in populations and maintains the same trends seen with adiponectin. The ratio increase with disease. HMW/total adiponectin decreases with high HbA1c (See Table 3). Again the, Type 1 diagnosis is less correlated with higher HMW/total adiponectin than a Type 2 diagnosis. However Type 1 diabetes diagnosis gave a higher ratio than normal controls.

The total levels of soluble C terminal AdipoR1 increases with diabetes pathology (e.g. type 2 diabetes or insulin resistance). These differences are much more significant than for adiponectin or the HMW ratio (T value>3.8, Probability of >99.9% significance) (See Table 4). Surprisingly, AdipoR1 increases with Type 1 diabetes indicating receptor is also related to Type 1. These patients would also be expected to suffer from adipocyte in balance, but also have beta cell loss. AdipoR1 increases more with higher HbA1c that adiponectin. Overall, AdipoR1 is more sensitive than adiponectin and the HMW ratio. The combination of AdipoR1 and adiponectin in a mathematical relationship was better than adiponectin alone at predicting diabetes pathology. The combination of AdipoR1 and c-peptide in a mathematical relationship was also was better than c-peptide alone at predicting diabetes pathology.

TABLE 2

Adiponectin

| | Total Count | Adiponectin (ug/mL) plasma Average | SD | T- value |
|---|---|---|---|---|
| Normal by medical history | 50 | 7.8 | 4.7 | |
| HbA1c <7 (only diabetics) | 40 | 8.2 | 10.0 | −0.1 |
| HbA1c 7 to 10 (only diabetics) | 26 | 6.8 | 5.2 | 0.9 |
| HbA1c >10 (only diabetics) | 3 | 8.4 | 1.4 | −0.1 |
| Type 1 by diagnosis | 13 | 10.0 | 7.1 | −1.3 |
| Type 2 by diagnosis | 56 | 7.1 | 8.3 | 0.6 |

TABLE 3

HMW/adiponectin

| | Total Count | HMW/total Adiponectin (ug/ug) Average | SD | T- value |
|---|---|---|---|---|
| Normal by medical history | 50 | 0.390 | 0.266 | |
| HbA1c <7 (only diabetics) | 40 | 0.926 | 2.553 | −1.3 |
| HbA1c 7 to 10 (only diabetics) | 26 | 0.551 | 0.342 | −1.8 |
| HbA1c >10 (only diabetics) | 3 | 0.607 | 0.281 | −1.2 |
| Type 1 by diagnosis | 13 | 0.529 | 0.277 | −1.7 |
| Type 2 by diagnosis | 56 | 0.830 | 2.137 | −1.4 |

TABLE 4 soluble AdipoR1

| | Total Count | sADIPOR1 (relative units) Average | SD | T- value |
|---|---|---|---|---|
| Normal by medical history | 50 | 16.2 | 4.3 | |
| HbA1c <7 (only diabetics) | 40 | 22.4 | 6.0 | −5.0 |
| HbA1c 7 to 10 (only diabetics) | 26 | 20.6 | 5.1 | −3.5 |
| HbA1c >10 (only diabetics) | 3 | 28.1 | 6.0 | −4.3 |
| Type 1 by diagnosis | 13 | 23.7 | 5.5 | −5.3 |
| Type 2 by diagnosis | 56 | 21.3 | 5.7 | −5.2 |

Example 2

Detection of C-Terminal Fragments in Individuals Having Metabolic Syndromes and Other Cardiovascular and Coronary Disorders Another group of 188 patients were fully characterized for cardiovascular conditions and risk by various diagnostic test and angiograph. Normals (n=113) were considered those without metabolic syndrome, diabetes, acute coronary syndrome (ACS), AMI or CHF. Patients out of 188 group were placed into affected groups for metabolic syndrome, inflammatory markers, ACS, AMI and CHF, hypertension, obesity, lipidemia, inflammatory response and anti-inflammatory response. Acute coronary syndrome was defined as blockage>60% by angiograph evaluation with or without acute cardiac condition. Metabolic syndrome was defined by insulin resistant or more than two metabolic risk factors by WHO definition. Insulin resistant was accessed by diagnosis and diabetic medication. Metabolic risk factors include hypertension, lipidemia and obesity. Obesity was assessed by body mass index (BMI). Hypertension was assessed by blood pressure or medication. Lipidemia was assessed by lipid ratio or lipid lowering medication. Inflammation was access by white blood cell count or CRP. Anti-inflammatory status was access by immunoassay for urinary trypsin inhibitors in blood and urine (Bikunin and Uristatin immunoassay measurements). All patients were additional assessed by medical history and medication and characterized into affected groups accordingly.

Adiponectin, and HMW Adiponectin were measured using commercial ELISA kit. Cardiac markers were measures using the Centaur instrument (Bayer). The AdipoR1 ELISA assay described in Example 1 was used to measure all C-terminal fragments whether bound or unbound.

Adiponectin decreases with ASC and metabolic syndrome but the significance of the values were less than expected for 99.9% certain (See Table 5). Adiponectin was increased with CHF and MI which would interferes with the assessment. Adiponectin was also not very correlated with inflammatory status.

The total levels of soluble AdipoR1 in serum increases with ASC and metabolic syndrome and the significance of the values were highly significant (99.9% certain) and much more significant than that observed for adiponectin (See Table 6). Surprising AdipoR1 increases as conditions become more acute and as the inflammatory and anti-inflammatory response increase. AdipoR1 further predicted for metabolic syndrome. Soluble AdipoR1 was also found in urine and plasma to correlate with metabolic syndrome.

TABLE 5

Adiponectin

| | Total Count | Adiponectin (ug/mL) plasma Average | SD | T- value (2) |
|---|---|---|---|---|
| Normals | 113 | 10.3 | 7.0 | |
| ACS or Metabolic syndrome | 24 | 5.7 | 2.7 | 3.2 |
| Metabolic syndrome | 29 | 6.1 | 3.5 | 3.2 |
| ACS and no AMI or CHF | 36 | 7.1 | 6.7 | 2.5 |
| MI by diagnosis or TnI | 8 | 15.9 | 12.6 | 2.1 |
| CHF by diagnosis or BNP | 9 | 22.2 | 15.2 | 4.4 |
| 0-30% blockage by angiogram (1) | 32 | 7.8 | 8.0 | 1.7 |
| 30-60% blockage by angiogram (1) | 15 | 9.6 | 8.2 | 0.4 |
| 60-100% blockage by angiogram (1) | 40 | 7.6 | 7.8 | 2.1 |
| Hypertension | 52 | 9.0 | 7.9 | 1.1 |
| Obesity | 60 | 7.1 | 6.0 | 3.1 |
| Lipidemia | 17 | 5.5 | 2.5 | 2.8 |
| Inflammatory response | 31 | 7.7 | 7.3 | 1.8 |
| Anti-inflammatory response | 33 | 8.7 | 8.2 | 1.2 |

(1) Includes patients with AMI and CHF
(2) Significance is 99.9% prob or 0.01 two tail when T value is greater than >3.8

TABLE 6 soluble AdipoR1

| | Total Count | Adiponectin (ug/mL) plasma | SD | T- value (2) |
|---|---|---|---|---|
| Normals | 113 | 16.5 | 4.0 | |
| ACS or Metabolic syndrome | 24 | 24.6 | 5.4 | 8.3 |
| Metabolic syndrome | 29 | 29.9 | 10.0 | 11.2 |
| ACS and no AMI or CHF | 36 | 24.1 | 5.3 | 9.0 |
| MI by diagnosis or TnI | 8 | 30.5 | 8.1 | 8.7 |
| CHF by diagnosis or BNP | 9 | 22.0 | 4.2 | 3.9 |
| 0-30% blockage by angiogram(1) | 32 | 20.8 | 3.7 | 5.3 |
| 30-60% blockage by angiogram(1) | 15 | 27.4 | 5.4 | 9.4 |
| 60-100% blockage by angiogram(1) | 40 | 29.3 | 8.9 | 12.1 |
| Hypertension | 52 | 23.3 | 5.6 | 8.8 |
| Obesity | 60 | 23.3 | 6.8 | 8.3 |
| Lipidemia | 17 | 25.5 | 8.2 | 7.2 |
| Inflammatory response | 31 | 23.4 | 8.9 | 6.2 |
| Anti-inflammatory response | 33 | 22.0 | 4.8 | 6.5 |
| Normals | 113 | 16.5 | 4.0 | | includes AMI and CHF >2.4 is approximately 99% prob or 0.01 two tail, >3.8 is approximately 99.9% prob or 0.001 two tail Example 3

Elucidating Biochemical Pathway

Normal insulin sensitivity results when insulin causes fat cell to produce adiponectin. Full length adiponectin aggregates into multimers, typically called LMW, MMW and HMW forms. Adiponetin interacts with the adiponectin receptor 2 in the liver and adiponectin receptor 1 in the muscle to stop glucose production and cause glycolysis and fatty acid oxidation. The adiponectin receptor 1 reacts with a cleaved form of adiponectin called globular adiponectin where as adiponectin receptor 2 reacts to full length adiponectin. Globular adiponectin was recently shown by others to form by action of blood elastase.

Insulin resistance occurs when adipocytes become hypertropic and produce less adiponectin in response to insulin. In this state, the cells become more apoptotic and cell division slows. As a result plasma adiponectin levels decreases. Insulin levels rise in an effort to cause cells to release more adiponectin. However as the insulin resistance worsens more insulin and less adiponectin is produced. The lesser adiponectin results in less glycolysis and fatty acid oxidation in muscle and prevents liver glucose production from stopping.

It was confirmed that inflammatory elastase and white blood cells are significantly elevated in diabetes patients. A review of the literature agreed that that both man made insulin and natural insulin increase white blood cells in diabetics. As elastase increases in inflammation, a higher percentage of globular adiponectin is produced. The lack of multimers causes less action on the liver. It was confirmed that anti-inflammatory protease inhibitors (Uri and Bik) were significantly elevated in diabetes. These inhibitors are formed by elastase and were recently shown in our cell models to induce hypertropic apoptosis in normal cell lines.

The receptor fragments after elastase exposure was proposed as mechanism for the formation of the soluble fragment in patient samples. This was tested using affinity mass spectroscopy with a polyclonal antibody for the AdipoR1 C terminal and patient samples.

The AdipoR1 was confirmed by mass spectra to be in blood with a mass of 34, 28-29, 19-18, 15-13, 9.5-9.0, 7.9, 6.6, 6.5, 5.2, 4.0 to 3.8 and 1 to 2 kDa. This data confirmed that 1) AdipoR1 fragments were found in patients and controls 2) AdipoR1 fragments form dimmers and 3) AdipoR1 fragments were bound to adiponectin. The last was proven by repeating the affinity mass spectroscopy with a polyclonal antibody for the adiponectin.

The lack of multimer adiponectin during insulin resistance was further proposed to the potential cause of differences in fragmentation patterns between patients and normals. Indeed a disappearance of the 3.9 and 7.8 masses forms occurred in diabetics but were present in all normals. In the data below, all 5 patient lacked these masses and all 5 normal had the 3901 and 7814 Da masses (see graph data). Therefore, different masses thought to be due to exposure of proteolytic cleave sites when there is availability of multimers for binding.

Example 4

Preparation of Monoclonal Antibodies

BALB/c mice were immunized with 100 µg/mouse of synthetic AdipoR1 peptide immunogen composition. After one month, ocular bleeds were taken from each mouse and titered by ELISA against the immunogen to assess the immune response. The mice showing the best response were boosted by injection of 100 µg/mouse with the immunogen. After four days, mice were sacrificed and their spleens used for fusion according to the method of Kohler and Milstein, Nature 256: 495 (1975). The spleenocytes were fused with SP2-0 Ag14 myeloma cells using PEG (polyethylene glycol) solution with a ratio of spleenocytes to Myeloma cells of 5:1 and plated into 96 well plates using 50% PEG/HAT growth media. After 7-10 days of incubation at 37 degrees Celsius, fusion cultures were monitored for growth by feeding every 3-4 days utilizing the HAT (hypoxanthine, aminopterin, thymidine) selection method followed by subculturing with HAT growth media.

After 2-3 weeks, the wells having hybridoma colony growth were tested by ELISA to determine which growths produced an antibody immune response to the peptide. The 96 well plate cultures were tested with the uristatin peptide at 1 ug/mL coated plates. After coating plates overnight at 2-8° C., all plates were washed and blocked. Cell culture supernatants were then applied 100 µl/well for one hour at room temperature. After washing plates, Goat anti-mouse IgG Horse Radish Peroxidase at 1:2000 dilution was applied at 100 uL/well for one hour. Plates were washed once again followed by OPD (o-phenylene diamine dihydrochloride) substrate and read at 490 nm on a Spectra Max plate reader.

The colonies giving a positive response were transferred to 24 well plates for further expansion and retesting to verify the positive results. The colonies testing positive were further expanded in six well plates in Iscove's Modified Dulbecco's Medium (IMDM) with 10% Fetal Bovine Serum (FBS). After expansion, the colonies were frozen at −70° C. and then transferred to liquid nitrogen for long-term storage. Based on ELISA results using the purified peptide, various clones were further expanded in IMDM, 10% FBS and frozen down.

Example 5

Characterization of Monoclonal Antibodies with SELDI

A method of measuring the specific adipoR1 fragments in patient samples was done using monoclonal antibodies and rabbit polyclonal antibodies were tested with soluble AdipoR standards and patients' plasmas on chip surfaces. The binding was estimated by Surface-Enhanced Laser Desorption/Ionization (SELDI) analysis on a SELDI PBS II time of flight mass spectrometer (Ciphergen, Fremont, Calif.) to determine the mass to charge ratios (m/z) for the proteins binding to the antibodies. Ten plasma specimens from patients were tested further: five patients were positive for diabetes; five patients were negative for diabetes. Binding was measured on two types of surfaces (PS20 and RS100) using a standard incubation procedure. The signal for each mass measurement was compared to the background noise to obtain the signal to noise ratios (S/N). Only masses with S/N ratios greater than 10 were accepted.

The SELDI procedure was as follows: Three microliter of 50 mmol/L $NaHCO_3$ (pH 8.0) was added to each spot on the protein chip and covered with a plate (i.e. a bioprocessor) to form sample wells followed by the addition of 1 µL antibody (1 mg/mL) to each spot and incubated at room temperature for 2 hours with shaking in a controlled-humidity chamber. The solution from each spot at that time was washed twice with 5 µL of washing buffer (phosphate buffered saline (PBS)+0.5% Triton detergent). The unbound sites were blocked with 5 µL of either 2 mg/mL BSA (bovine serum albumin) or 1 mol/L ethanolamine. After incubation at room temperature the BSA or ethanolamine was discarded and the spots were washed twice with 5 µL of washing buffer (PBS+0.5% Triton). Five µL of PBS was added to each spot and the chips were placed into the bioprocessor. An additional 10 µL PBS as well as 10 µL of the sample to be tested (or PBS as a control) were added to each well, followed by shaking the sealed wells at 4° C. for 18 hours. The wells were then washed with washing buffer and PBS and again shaken at room temperature for 2 min. The wells were rinsed twice with 300 µL of deionized water saturated with sinapinic acid; this serves as an energy-absorbing molecule during protonation of proteins bound to the antibodies. The latter are attached to the surface of the chips. The chips containing the antibody-bound specimens were analyzed for binding mass using the SELDI mass spectrometer according to the manufacturer's instructions.

Example 6

Soluble C Terminal Fragments in Diabetics

Table 6 shows the results of multiple determinations for five normal patients for the detection of an adiponectin receptor fragment mass of 7812 and five diabetics not having the same mass. A similar separation was found for a mass of 3901. These two masses are present in normal subjects but absent or present in very low levels, i.e., decreased levels in subjects having the disease conditions provided herein.

TABLE 6

SELDI results at 7812 and 3901 daltons

| Patient condition | Number of patients | Number of patients with Masses at 3901 | Number of patients Masses at 7812 |
| --- | --- | --- | --- |
| Diabetics | 5 | 0 | 0 |
| Non-diabetics | 5 | 5 | 5 |

Table 7 shows the results of multiple determinations for five normal and diabetic patients for the detection of adiponectin receptor fragments having masses of 4.5-6.9, 7-8.2, 9-11, 13-15, 17-19, 27-29, or 30-34 and five diabetics not having the same masses.

TABLE 7

SELDI results at 4.5-6.9, 7-8.2, 9-11, 13-15, 17-19, 27-29, or 30-34 KDa daltons

| Patient condition | Number of patients | Number of patients with 4.5-6.9, 7-8.2, 9-11, 13-15, 17-19, 27-29, or 30-34 KDa | Number of patients with increases in the amount of 4.5-6.9, 7-8.2, 9-11, 13-15, 17-19, 27-29, or 30-34 KDa |
|---|---|---|---|
| Diabetics | 5 | 5 | 5 |
| Non-diabetics | 5 | 5 | 5 |

Example 7

Serine Proteases

Trypsin family serine proteases are increased during inflammation and include trypsin, chymotrypsin, kallikrein, plasmin, complement D, thrombin, and Factors IX a, Xa, XIa and XIIa. All have tryptase primary affinity cleaving Arg-Xaa or Lys-Xaa. Additional rrypsin family serine proteases released by immune cells include elastase, granzyme (A, B, H, M), tryptase 2 and mast cell proteases 1. The key elastase homologues including cathepsin G, proteinase 3, azurocidin and mycolobastin have Val-Xaa>Ala-Xaa cleaving affinity. Granzymes A and K have tryptase cleaving affinity. Granzyme B has aspase cleaving affinity for Asp-Xaa. Granzyme M has metase cleaving affinity for Met-Xaa or Leu-Xaa. Granzyme H and Mast cell protease 1 have chymase cleaving affinity for cleaving Phe-Xaa, Tyr-Xaa, or Trp-Xaa.

Analysis of fragmentation patterns for adiponectin and adiponectin receptor fragments were determined using trypsin and elastase as example inflammatory proteases. The fragments that are 29 to 34 amino acid in length (i.e., SEQ ID NOS: 1, 2, 4-11, 16, 17, and/or 19-26) were predicted by elastase cleavage. The fragments that are 20 to 25 amino acids in length (i.e., SEQ ID NOS: 3, 12-15, 18, and/or 27-30) were predicted by general trypsin family serine proteases or granzyme.

Example 8

Setting Sensitivity and Specificity

The samples are divided between normal and abnormal. Results are collected for all and the observed adipoR1 values are judged against an assigned adipoR1 threshold. The threshold is the value below which all results are considered normal and above which results are considered positive. The threshold is varied from a low number to a high number and the predictive value of the result is calculated, using the number of true positives, false positive, true negatives and false negatives found. The sensitivity (TP/TP+FP) and specificity (TN/TN+FN) are calculated for each threshold tested. The threshold with the highest sensitivity and specificity gives the best predictive value. (100% would be ideal).

Example 9

Adiponectin Receptor Fragment Thresholds

The following is an example of setting threshold using the patients and methods shown in example 1. In the table below, the threshold above which AdipoR1 result was considered positive is varied from 15 to 21 ug/mL. In this example, a higher value is considered a positive. The number of true negatives, or correctly identified patients without diagnosed diabetes, is calculated along with the number of false positives, false negatives and true positive. Ideally, an assay would have no false positives or 100% specificity and no false negatives or 100% sensitivity. As can be seen from the data, the threshold of 15 was better for sensitivity while the threshold of 21 was better for specificity. The threshold and range are dependent on the fragment detected and analytical method used. In this example the total assay range was 5 to 30 ug/mL or approximately 6×. Accordingly, the concentration units and range varied with the fragment detected and analytical method used (SELDI vs ELISA). For example, for the fragment tested in Example 6 and Table 7, the difference between normals and diabetic was often 100×. As expected, the concentration for one specific fragment was less than the concentration of all fragments. The type of sample used, whether urine, plasma or serum also impacted the concentrations of fragment. Urine and serum had fragment concentration about 10 fold lower than plasma. Once an assay and fragment is selected, the thresholds are adjusted to best achieve the clinical agreement desired, using the methods shown.

TABLE 8

| AdipoR1 Threshold | True Negative (TN) | False Positive (FP) | True Positive (TP) | False Negative (FN) |
|---|---|---|---|---|
| >=15 ug/mL | 19 | 31 | 62 | 7 |
| >=16 | 22 | 28 | 58 | 11 |
| >=17 | 26 | 24 | 54 | 15 |
| >=18 | 33 | 17 | 50 | 19 |
| >=19 | 39 | 11 | 45 | 24 |
| >=20 | 43 | 7 | 41 | 28 |
| >=21 | 44 | 6 | 37 | 32 |

Example 10

Use of Panels for Adipocyte Imbalance Assays

The following is an example of using additional and related biomarkers with the AdipoR1 result to improve the prediction of diabetic disorder. The diabetic and normal patients and methods shown in example 1 are used. In the table below, three analyte are compared for their ability to detect diabetes. The thresholds used offered comparable TN. As expected, ADIPOR1 detected more true positives than the other analyes.

TABLE 9

| Analyte | Threshold used to define positive | TN | FP | TP | FN | Type 1 neg | Type 1 pos |
|---|---|---|---|---|---|---|---|
| Adiponectin | <=4 ug/mL | 46 | 4 | 24 | 45 | 21 | 4 |
| c-peptide | <300 pmol/L | 41 | 9 | 10 | 59 | 6 | 19 |

TABLE 9-continued

| Analyte | Threshold used to define positive | TN | FP | TP | FN | Type 1 neg | Type 1 pos |
|---|---|---|---|---|---|---|---|
| c-peptide | >2700 pmol/L | 48 | 2 | 21 | 48 | 23 | 2 |
| AdipoR1 | >=21 ug/mL | 44 | 6 | 37 | 32 | 15 | 10 |

Twenty five of the sixty-nine diabetics were Type 1. The analytes were also compared for the ability to be positive for type 1 diabetes. Only 4 of the 25 type 1 diabetics had an abnormally low adiponectin. C-peptide uses two thresholds, one for abnormally low and one for abnormally high levels. An abnormally low c-peptide, indicates a lack of insulin and as expected 23 of the 25 type 1 diabetic had abnormally low c-peptide. Type 1 diabetics also often had AdipoR1 fragments. Few type 1 diabetics had abnormally high c-peptide.

These analytes detect different patients. This is likely explained by differences in the pathology, as the each analyte measures a different part of the imbalance. For example, it is believed that the lack of insulin impacting c-peptide is due to the islet cells whereas the lack of adiponectin is due to the adipocytes failing to produce the hormone. The presence of adipoR1 fragments in this example is believed to be due to muscle cell shedding the receptor from over use.

This data demonstrates that the combination of the analytes together could be better than any one alone. In the table below, the simplest of relationships is tested by considering any one of the panel positive to mean that the result is abnormal. Accordingly all analytes must be negative to be considered a normal result. As described above, thresholds are adjusted to achieve the best results.

TABLE 10

| ADIPOR1 | C-peptide High abnormal | C-peptide Low abnormal | Adiponectin | TN | FP | TP | FN |
|---|---|---|---|---|---|---|---|
| >=21 | >=2700 | Not used | Not used | 43 | 7 | 47 | 22 |
| >=21 | >=2700 | <=300 | Not used | 34 | 5 | 37 | 18 |
| >=21 | Not used | Not used | <=4 | 34 | 16 | 50 | 19 |
| >=21 | >=2700 | Not used | <=4 | 41 | 9 | 53 | 16 |

The highest number of true positives was obtained for the combined use of c-peptide, adiponectin and adipoR1. The highest number of true negatives was obtained for the combined use of c-peptide and adipoR1 or by the use c-peptide, adiponectin and adipoR1. In both cases, the numbers of true negatives were comparable to the adipoR1.

Example 11

Soluble Adiponectin Receptor 1 Levels in Plasma of CAD Patents

The following is an example of using additional and related biomarkers with the AdipoR1 result to improve the prediction of cardiovascular disorder. The cardiovascular disorder and normal patients and methods shown in example 2 are used. Affect patients were those with ACS by angiograph or high risk by meeting the definition of metabolic syndrome. Patients with pre-existing cardiovascular conditions such AMI and CHF were excluded as a diagnosis would already be made by the TnI or BNP assays or other diagnostic assessments.

Adiponectin receptor 1 soluble C terminal fragments were measured by ELISA as shown in Example 1. The results correlated well with degrees of vascular blockage (Table 11) Risk of cardiovascular disorders was also assessed by additional marker for pro and anti-inflammatory response and adiponectin. Analytes for pro and anti-inflammatory response were compared to the adipor1. Abnormal AdipoR results were more likely present in patients with vascular blockage than adiponectin, uristatin, bikunin, WBC or CRP. The higher sensitivity supports a diagnostic correlation of adiponectin receptor 1 for vascular blockage due to atherosclerosis.

TABLE 11

Sensitivity of Adiponectin Receptor 1 soluble fragments for atherosclerosis

| Marker | Specificity (%) | Sensitivity (%) |
|---|---|---|
| Bikunin | 95 | 25 |
| Uristatin | 95 | 25 |
| CRP | 95 | 15 |
| WBC - total | 80 | 25 |
| WBC - gran | 85 | 25 |
| Bikunin and uristatin | 90 | 45 |
| Lipid Risk Ratio | 95 | 20 |
| Adiopnectin | 85 | 20 |
| Soluble AdipoR1 in plasma | 85 | 75 |

The use of panels of pro and anti-inflammatory response and adipocyte markers were compared for there ability to detect cardiovascular disorders. The highest number of true positive was obtained for the combined use of Bikunin, uristatin, CRP, WBC, adiponectin and adipoR1. The highest number of true negative was obtained for the combined use of adiponectin and adipoR1.

Each recited range includes all combinations and sub-combinations of ranges, as well as specific numerals contained therein.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A method for detecting a condition characterized by an adipocyte imbalance or determining progression or regression of a condition characterized by an adipocyte imbalance or efficacy of treatment of a condition characterized by an adipocyte imbalance in a subject, wherein said condition is diabetes type I, diabetes type II, insulin resistance, metabolic syndrome, cardiovascular disease, vascular blockage, or arteriosclerosis, said method comprising:

determining the level of at least one soluble C-terminal fragment of the adiponectin receptor, wherein said at least one soluble C-terminal fragment of the adiponectin receptor is a 13 to 34 amino acid peptide comprising the amino acid sequence of any one of SEQ ID NOs: 1 to 44 or an amino acid sequence having at least 80% identity of any one of SEQ ID NOs: 1 to 44, present in a biological sample obtained from the subject and correlating the level with presence or absence of the condition, progression of the condition, or efficacy of treatment of the condition, wherein an increase in the total level of said at least one soluble C-terminal fragment of the adiponectin receptor in said biological sample relative to a control sample of a subject not suffering from said condition or to a diagnostic threshold for said condition is indicative of said test subject having said condition;

wherein an increase in the total level of said at least one soluble C-terminal fragment of the adiponectin receptor in said biological sample relative to a biological sample of said subject obtained at an earlier point in time is indicative of progression of said condition;

wherein a decrease in the total level of said at least one soluble C-terminal fragment of the adiponectin receptor in said biological sample relative to a biological sample of said subject obtained at an earlier point in time is indicative of regression of said condition; and wherein a decrease in the total level of said at least one soluble C-terminal fragment of the adiponectin receptor in said biological sample after treatment relative to the level of said at least one soluble C-terminal fragment of the adiponectin receptor in a biological sample obtained from said subject at an earlier point in time is indicative of efficacy of treatment of said condition in said test subject.

2. The method of claim 1 wherein the at least one soluble C-terminal fragment is bound to carrier protein.

3. The method of claim 2, wherein said carrier protein comprises adiponectin or an adiponectin fragment.

4. The method of claim 2 wherein the at least one C-terminal fragment bound to carrier protein is detected by an antibody.

5. The method of claim 1 wherein the at least one soluble C-terminal fragment is unbound.

6. The method of claim 1 further comprising determining the level of adiponectin in a biological sample obtained from the subject and correlating the level of adiponectin with presence or absence of the condition, progression or regression of the condition, or efficacy of treatment of the condition.

7. The method of claim 1 further comprising determining the level of bikunin in a biological sample obtained from the subject and correlating the level of bikunin with presence or absence of the condition, progression or regression of the condition, or efficacy of treatment of the condition.

8. The method of claim 1 further comprising determining the level of C-reactive protein in a biological sample obtained from the subject and correlating the level of C-reactive protein with presence or absence of the condition, progression or regression of the condition, or efficacy of treatment of the condition.

9. The method of claim 1 further comprising determining the level of white blood cells in a biological sample obtained from the subject and correlating the level of white blood cells with presence or absence of the condition, progression or regression of the condition, or efficacy of treatment of the condition.

10. The method of claim 1 further comprising determining the level of c-peptide in a biological sample obtained from the subject and correlating the level of c-peptide with presence or absence of the condition, progression or regression of the condition, or efficacy of treatment of the condition.

11. The method of claim 1 wherein the method is for detecting the condition characterized by an adipocyte imbalance.

12. The method of claim 1 wherein the method is for determining progression or regression of the condition characterized by an adipocyte imbalance.

13. The method of claim 1 wherein the method is for determining efficacy of treatment of the condition characterized by an adipocyte imbalance.

14. The method of claim 13 wherein the treatment is administration of a peroxisome proliferator-activated receptor (PPAR) gamma agonist.

15. The method of claim 1 wherein the cardiovascular disease is congestive heart failure, acute myocardial infarction, coronary artery disease, atherosclerosis, or ischemia.

16. The method of claim 1 wherein the step of determining the level of the at least one soluble C-terminal fragment of the adiponectin receptor present in the biological sample comprises contacting the biological sample with a binding agent specific for the at least one soluble C-terminal fragment of the adiponectin receptor.

17. The method of claim 16 wherein the binding agent specific for the at least one soluble C-terminal fragment of the adiponectin receptor is an antibody.

18. The method of claim 16 wherein the binding agent is labeled with a reporter molecule.

19. The method of claim 16 wherein said step of determining the level of the at least one C-terminal fragment of the adiponectin receptor present in the biological fluid sample further comprises contacting the biological sample with a second binding agent specific for the binding agent specific for the at least one C-terminal fragment of the adiponectin receptor.

20. The method of claim 19 wherein the second binding agent is labeled with a reporter molecule.

21. The method of claim 19 wherein the second binding agent specific for the binding agent specific for the at least one C-terminal fragment of the adiponectin receptor is an antibody.

22. The method of claim 1 wherein the biological sample is blood plasma, whole blood, or urine.

23. The method of claim 1 wherein said step of determining the level of said at least one soluble C-terminal fragment of the adiponectin receptor comprises an enzyme-linked immunosorbent assay (ELISA) or mass spectrometry.

24. The method of claim 23 wherein said mass spectrometry comprises surface-enhanced laser desorption/ionization (SELDI).

* * * * *

SEQUENCE LISTING

<160> NUMBER OF SEQ ID NOS: 50

<210> SEQ ID NO 1
<211> LENGTH: 34
<212> TYPE: PRT

```
<213> ORGANISM: Artificial Sequence
<220> FEATURE:
<223> OTHER INFORMATION: Synthetic construct

<400> SEQUENCE: 1

Val Leu Val Val Ala Ala Phe Val His Phe Tyr Gly Val Ser Asn
1               5                   10                  15

Leu Gln Glu Phe Arg Tyr Gly Leu Glu Gly Gly Cys Thr Asp Asp Thr
            20                  25                  30

Leu Leu

<210> SEQ ID NO 2
<211> LENGTH: 33
<212> TYPE: PRT
<213> ORGANISM: Artificial Sequence
<220> FEATURE:
<223> OTHER INFORMATION: Synthetic construct

<400> SEQUENCE: 2

Leu Val Val Ala Ala Ala Phe Val His Phe Tyr Gly Val Ser Asn Leu
1               5                   10                  15

Gln Glu Phe Arg Tyr Gly Leu Glu Gly Gly Cys Thr Asp Asp Thr Leu
            20                  25                  30

Leu

<210> SEQ ID NO 3
<211> LENGTH: 20
<212> TYPE: PRT
<213> ORGANISM: Artificial Sequence
<220> FEATURE:
<223> OTHER INFORMATION: Synthetic construct

<400> SEQUENCE: 3

Ser Asn Leu Gln Glu Phe Arg Tyr Gly Leu Glu Gly Gly Cys Thr Asp
1               5                   10                  15

Asp Thr Leu Leu
            20

<210> SEQ ID NO 4
<211> LENGTH: 32
<212> TYPE: PRT
<213> ORGANISM: Artificial Sequence
<220> FEATURE:
<223> OTHER INFORMATION: Synthetic construct

<400> SEQUENCE: 4

Val Val Ala Ala Ala Phe Val His Phe Tyr Gly Val Ser Asn Leu Gln
1               5                   10                  15

Glu Phe Arg Tyr Gly Leu Glu Gly Gly Cys Thr Asp Asp Thr Leu Leu
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Synthetic construct

<400> SEQUENCE: 5

Val Ala Ala Ala Phe Val His Phe Tyr Gly Val Ser Asn Leu Gln Glu
1               5                   10                  15

Phe Arg Tyr Gly Leu Glu Gly Gly Cys Thr Asp Asp Thr Leu Leu
            20                  25                  30
```

```
<210> SEQ ID NO 6
<211> LENGTH: 30
<212> TYPE: PRT
<213> ORGANISM: Artificial Sequence
<220> FEATURE:
<223> OTHER INFORMATION: Synthetic construct

<400> SEQUENCE: 6

Ala Ala Ala Phe Val His Phe Tyr Gly Val Ser Asn Leu Gln Glu Phe
 1               5                  10                  15

Arg Tyr Gly Leu Glu Gly Gly Cys Thr Asp Asp Thr Leu Leu
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: Synthetic construct

<400> SEQUENCE: 7

Ala Ala Phe Val His Phe Tyr Gly Val Ser Asn Leu Gln Glu Phe Arg
 1               5                  10                  15

Tyr Gly Leu Glu Gly Gly Cys Thr Asp Asp Thr Leu Leu
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct

<400> SEQUENCE: 8

Ala Phe Val His Phe Tyr Gly Val Ser Asn Leu Gln Glu Phe Arg Tyr
 1               5                  10                  15

Gly Leu Glu Gly Gly Cys Thr Asp Asp Thr Leu Leu
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic construct

<400> SEQUENCE: 9

Phe Val His Phe Tyr Gly Val Ser Asn Leu Gln Glu Phe Arg Tyr Gly
 1               5                  10                  15

Leu Glu Gly Gly Cys Thr Asp Asp Thr Leu Leu
            20                  25

<210> SEQ ID NO 10
<211> LENGTH: 26
<212> TYPE: PRT
<213> ORGANISM: Artificial Sequence
<220> FEATURE:
<223> OTHER INFORMATION: Synthetic construct

<400> SEQUENCE: 10

Val His Phe Tyr Gly Val Ser Asn Leu Gln Glu Phe Arg Tyr Gly Leu
 1               5                  10                  15

Glu Gly Gly Cys Thr Asp Asp Thr Leu Leu
            20                  25
```

<210> SEQ ID NO 11
<211> LENGTH: 25
<212> TYPE: PRT
<213> ORGANISM: Artificial Sequence
<220> FEATURE:
<223> OTHER INFORMATION: Synthetic construct

<400> SEQUENCE: 11

His Phe Tyr Gly Val Ser Asn Leu Gln Glu Phe Arg Tyr Gly Leu Glu
1               5                   10                  15

Gly Gly Cys Thr Asp Asp Thr Leu Leu
            20                  25

<210> SEQ ID NO 12
<211> LENGTH: 24
<212> TYPE: PRT
<213> ORGANISM: Artificial Sequence
<220> FEATURE:
<223> OTHER INFORMATION: Synthetic construct

<400> SEQUENCE: 12

Phe Tyr Gly Val Ser Asn Leu Gln Glu Phe Arg Tyr Gly Leu Glu Gly
1               5                   10                  15

Gly Cys Thr Asp Asp Thr Leu Leu
            20

<210> SEQ ID NO 13
<211> LENGTH: 23
<212> TYPE: PRT
<213> ORGANISM: Artificial Sequence
<220> FEATURE:
<223> OTHER INFORMATION: Synthetic construct

<400> SEQUENCE: 13

Tyr Gly Val Ser Asn Leu Gln Glu Phe Arg Tyr Gly Leu Glu Gly Gly
1               5                   10                  15

Cys Thr Asp Asp Thr Leu Leu
            20

<210> SEQ ID NO 14
<211> LENGTH: 22
<212> TYPE: PRT
<213> ORGANISM: Artificial Sequence
<220> FEATURE:
<223> OTHER INFORMATION: Synthetic construct

<400> SEQUENCE: 14

Gly Val Ser Asn Leu Gln Glu Phe Arg Tyr Gly Leu Glu Gly Gly Cys
1               5                   10                  15

Thr Asp Asp Thr Leu Leu
            20

<210> SEQ ID NO 15
<211> LENGTH: 21
<212> TYPE: PRT
<213> ORGANISM: Artificial Sequence
<220> FEATURE:
<223> OTHER INFORMATION: Synthetic construct

<400> SEQUENCE: 15

Val Ser Asn Leu Gln Glu Phe Arg Tyr Gly Leu Glu Gly Gly Cys Thr
1               5                   10                  15

Asp Asp Thr Leu Leu
            20

```
<210> SEQ ID NO 16
<211> LENGTH: 19
<212> TYPE: PRT
<213> ORGANISM: Artificial Sequence
<220> FEATURE:
<223> OTHER INFORMATION: Synthetic construct

<400> SEQUENCE: 16

Asn Leu Gln Glu Phe Arg Tyr Gly Leu Glu Gly Gly Cys Thr Asp Asp
1               5                   10                  15

Thr Leu Leu

<210> SEQ ID NO 17
<211> LENGTH: 18
<212> TYPE: PRT
<213> ORGANISM: Artificial Sequence
<220> FEATURE:
<223> OTHER INFORMATION: Synthetic construct

<400> SEQUENCE: 17

Leu Gln Glu Phe Arg Tyr Gly Leu Glu Gly Gly Cys Thr Asp Asp Thr
1               5                   10                  15

Leu Leu

<210> SEQ ID NO 18
<211> LENGTH: 17
<212> TYPE: PRT
<213> ORGANISM: Artificial Sequence
<220> FEATURE:
<223> OTHER INFORMATION: Synthetic construct

<400> SEQUENCE: 18

Gln Glu Phe Arg Tyr Gly Leu Glu Gly Gly Cys Thr Asp Asp Thr Leu
1               5                   10                  15

Leu

<210> SEQ ID NO 19
<211> LENGTH: 16
<212> TYPE: PRT
<213> ORGANISM: Artificial Sequence
<220> FEATURE:
<223> OTHER INFORMATION: Synthetic construct

<400> SEQUENCE: 19

Glu Phe Arg Tyr Gly Leu Glu Gly Gly Cys Thr Asp Asp Thr Leu Leu
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic construct

<400> SEQUENCE: 20

Phe Arg Tyr Gly Leu Glu Gly Gly Cys Thr Asp Asp Thr Leu Leu
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Synthetic construct

<400> SEQUENCE: 21
```

```
Arg Tyr Gly Leu Glu Gly Gly Cys Thr Asp Asp Thr Leu Leu
1               5                   10
```

<210> SEQ ID NO 22
<211> LENGTH: 13
<212> TYPE: PRT
<213> ORGANISM: Artificial Sequence
<220> FEATURE:
<223> OTHER INFORMATION: Synthetic construct

<400> SEQUENCE: 22

```
Tyr Gly Leu Glu Gly Gly Cys Thr Asp Asp Thr Leu Leu
1               5                   10
```

<210> SEQ ID NO 23
<211> LENGTH: 34
<212> TYPE: PRT
<213> ORGANISM: Artificial Sequence
<220> FEATURE:
<223> OTHER INFORMATION: Synthetic construct

<400> SEQUENCE: 23

```
Ile Phe Val Val Ala Gly Ala Phe Val His Phe His Gly Val Ser Asn
1               5                   10                  15

Leu Gln Glu Phe Arg Phe Met Ile Gly Gly Gly Cys Ser Glu Glu Asp
            20                  25                  30

Ala Leu
```

<210> SEQ ID NO 24
<211> LENGTH: 31
<212> TYPE: PRT
<213> ORGANISM: Artificial Sequence
<220> FEATURE:
<223> OTHER INFORMATION: Synthetic construct

<400> SEQUENCE: 24

```
Val Ala Gly Ala Phe Val His Phe His Gly Val Ser Asn Leu Gln Glu
1               5                   10                  15

Phe Arg Phe Met Ile Gly Gly Gly Cys Ser Glu Glu Asp Ala Leu
            20                  25                  30
```

<210> SEQ ID NO 25
<211> LENGTH: 20
<212> TYPE: PRT
<213> ORGANISM: Artificial Sequence
<220> FEATURE:
<223> OTHER INFORMATION: Synthetic construct

<400> SEQUENCE: 25

```
Ser Asn Leu Gln Glu Phe Arg Phe Met Ile Gly Gly Gly Cys Ser Glu
1               5                   10                  15

Glu Asp Ala Leu
            20
```

<210> SEQ ID NO 26
<211> LENGTH: 33
<212> TYPE: PRT
<213> ORGANISM: Artificial Sequence
<220> FEATURE:
<223> OTHER INFORMATION: Synthetic construct

<400> SEQUENCE: 26

```
Phe Val Val Ala Gly Ala Phe Val His Phe His Gly Val Ser Asn Leu
1               5                   10                  15
```

Gln Glu Phe Arg Phe Met Ile Gly Gly Gly Cys Ser Glu Glu Asp Ala
            20                  25                  30

Leu

<210> SEQ ID NO 27
<211> LENGTH: 32
<212> TYPE: PRT
<213> ORGANISM: Artificial Sequence
<220> FEATURE:
<223> OTHER INFORMATION: Synthetic construct

<400> SEQUENCE: 27

Val Val Ala Gly Ala Phe Val His Phe His Gly Val Ser Asn Leu Gln
1               5                   10                  15

Glu Phe Arg Phe Met Ile Gly Gly Gly Cys Ser Glu Glu Asp Ala Leu
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic construct

<400> SEQUENCE: 28

Ala Gly Ala Phe Val His Phe His Gly Val Ser Asn Leu Gln Glu Phe
1               5                   10                  15

Arg Phe Met Ile Gly Gly Gly Cys Ser Glu Glu Asp Ala Leu
            20                  25                  30

<210> SEQ ID NO 29
<211> LENGTH: 29
<212> TYPE: PRT
<213> ORGANISM: Artificial Sequence
<220> FEATURE:
<223> OTHER INFORMATION: Synthetic construct

<400> SEQUENCE: 29

Gly Ala Phe Val His Phe His Gly Val Ser Asn Leu Gln Glu Phe Arg
1               5                   10                  15

Phe Met Ile Gly Gly Gly Cys Ser Glu Glu Asp Ala Leu
            20                  25

<210> SEQ ID NO 30
<211> LENGTH: 28
<212> TYPE: PRT
<213> ORGANISM: Artificial Sequence
<220> FEATURE:
<223> OTHER INFORMATION: Synthetic construct

<400> SEQUENCE: 30

Ala Phe Val His Phe His Gly Val Ser Asn Leu Gln Glu Phe Arg Phe
1               5                   10                  15

Met Ile Gly Gly Gly Cys Ser Glu Glu Asp Ala Leu
            20                  25

<210> SEQ ID NO 31
<211> LENGTH: 27
<212> TYPE: PRT
<213> ORGANISM: Artificial Sequence
<220> FEATURE:
<223> OTHER INFORMATION: Synthetic construct

<400> SEQUENCE: 31

Phe Val His Phe His Gly Val Ser Asn Leu Gln Glu Phe Arg Phe Met

```
                1               5                  10                  15
Ile Gly Gly Gly Cys Ser Glu Glu Asp Ala Leu
            20                  25
```

<210> SEQ ID NO 32
<211> LENGTH: 26
<212> TYPE: PRT
<213> ORGANISM: Artificial Sequence
<220> FEATURE:
<223> OTHER INFORMATION: Synthetic construct

<400> SEQUENCE: 32

```
Val His Phe His Gly Val Ser Asn Leu Gln Glu Phe Arg Phe Met Ile
1               5                  10                  15
Gly Gly Gly Cys Ser Glu Glu Asp Ala Leu
            20                  25
```

<210> SEQ ID NO 33
<211> LENGTH: 25
<212> TYPE: PRT
<213> ORGANISM: Artificial Sequence
<220> FEATURE:
<223> OTHER INFORMATION: Synthetic construct

<400> SEQUENCE: 33

```
His Phe His Gly Val Ser Asn Leu Gln Glu Phe Arg Phe Met Ile Gly
1               5                  10                  15
Gly Gly Cys Ser Glu Glu Asp Ala Leu
            20                  25
```

<210> SEQ ID NO 34
<211> LENGTH: 24
<212> TYPE: PRT
<213> ORGANISM: Artificial Sequence
<220> FEATURE:
<223> OTHER INFORMATION: Synthetic construct

<400> SEQUENCE: 34

```
Phe His Gly Val Ser Asn Leu Gln Glu Phe Arg Phe Met Ile Gly Gly
1               5                  10                  15
Gly Cys Ser Glu Glu Asp Ala Leu
            20
```

<210> SEQ ID NO 35
<211> LENGTH: 23
<212> TYPE: PRT
<213> ORGANISM: Artificial Sequence
<220> FEATURE:
<223> OTHER INFORMATION: Synthetic construct

<400> SEQUENCE: 35

```
His Gly Val Ser Asn Leu Gln Glu Phe Arg Phe Met Ile Gly Gly Gly
1               5                  10                  15
Cys Ser Glu Glu Asp Ala Leu
            20
```

<210> SEQ ID NO 36
<211> LENGTH: 22
<212> TYPE: PRT
<213> ORGANISM: Artificial Sequence
<220> FEATURE:
<223> OTHER INFORMATION: Synthetic construct

<400> SEQUENCE: 36

```
Gly Val Ser Asn Leu Gln Glu Phe Arg Phe Met Ile Gly Gly Gly Cys
```

```
                1               5                  10                  15
Ser Glu Glu Asp Ala Leu
            20

<210> SEQ ID NO 37
<211> LENGTH: 21
<212> TYPE: PRT
<213> ORGANISM: Artificial Sequence
<220> FEATURE:
<223> OTHER INFORMATION: Synthetic construct

<400> SEQUENCE: 37

Val Ser Asn Leu Gln Glu Phe Arg Phe Met Ile Gly Gly Gly Cys Ser
1               5                  10                  15

Glu Glu Asp Ala Leu
            20

<210> SEQ ID NO 38
<211> LENGTH: 19
<212> TYPE: PRT
<213> ORGANISM: Artificial Sequence
<220> FEATURE:
<223> OTHER INFORMATION: Synthetic construct

<400> SEQUENCE: 38

Asn Leu Gln Glu Phe Arg Phe Met Ile Gly Gly Gly Cys Ser Glu Glu
1               5                  10                  15

Asp Ala Leu

<210> SEQ ID NO 39
<211> LENGTH: 18
<212> TYPE: PRT
<213> ORGANISM: Artificial Sequence
<220> FEATURE:
<223> OTHER INFORMATION: Synthetic construct

<400> SEQUENCE: 39

Leu Gln Glu Phe Arg Phe Met Ile Gly Gly Gly Cys Ser Glu Glu Asp
1               5                  10                  15

Ala Leu

<210> SEQ ID NO 40
<211> LENGTH: 17
<212> TYPE: PRT
<213> ORGANISM: Artificial Sequence
<220> FEATURE:
<223> OTHER INFORMATION: Synthetic construct

<400> SEQUENCE: 40

Gln Glu Phe Arg Phe Met Ile Gly Gly Gly Cys Ser Glu Glu Asp Ala
1               5                  10                  15

Leu

<210> SEQ ID NO 41
<211> LENGTH: 16
<212> TYPE: PRT
<213> ORGANISM: Artificial Sequence
<220> FEATURE:
<223> OTHER INFORMATION: Synthetic construct

<400> SEQUENCE: 41

Glu Phe Arg Phe Met Ile Gly Gly Gly Cys Ser Glu Glu Asp Ala Leu
1               5                  10                  15
```

<210> SEQ ID NO 42
<211> LENGTH: 15
<212> TYPE: PRT
<213> ORGANISM: Artificial Sequence
<220> FEATURE:
<223> OTHER INFORMATION: Synthetic construct

<400> SEQUENCE: 42

Phe Arg Phe Met Ile Gly Gly Gly Cys Ser Glu Glu Asp Ala Leu
1               5                   10                  15

<210> SEQ ID NO 43
<211> LENGTH: 14
<212> TYPE: PRT
<213> ORGANISM: Artificial Sequence
<220> FEATURE:
<223> OTHER INFORMATION: Synthetic construct

<400> SEQUENCE: 43

Arg Phe Met Ile Gly Gly Gly Cys Ser Glu Glu Asp Ala Leu
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthetic construct

<400> SEQUENCE: 44

Phe Met Ile Gly Gly Gly Cys Ser Glu Glu Asp Ala Leu
1               5                   10

<210> SEQ ID NO 45
<211> LENGTH: 2108
<212> TYPE: DNA
<213> ORGANISM: Artificial Sequence
<220> FEATURE:
<223> OTHER INFORMATION: Oligonucleotide primer

<400> SEQUENCE: 45

| | | | | | |
|---|---|---|---|---|---|
| ggcgctgaag | atcggggccg | ctcggccgca | ggccgcctcc | agcgccgcgg | gatgtagcgc | 60 |
| ggggaccgc | ggcccccagc | agagcccgcc | tgcccggctt | gtctaccatc | agaggagat | 120 |
| ctctgccccc | tggggctgag | agaccccaac | ctttccccaa | gctgaagctg | cagggtattg | 180 |
| aggtaccagc | cagatgtctt | cccacaaagg | atctgtggtg | gcacagggga | atggggctcc | 240 |
| tgccagtaac | agggaagctg | acacggtgga | actggctgaa | ctgggacccc | tgctagaaga | 300 |
| gaagggcaaa | cgggtaatcg | ccaacccacc | caaagctgaa | gagagcaaa | catgcccagt | 360 |
| gccccaggaa | gaagaggagg | aggtgcgggt | actgacactt | cccctgcaag | cccaccacgc | 420 |
| catggagaag | atggaagagt | ttgtgtacaa | ggtctgggag | ggacgttgga | gggtcatccc | 480 |
| atatgatgtg | ctccctgact | ggctaaagga | caacgactat | ctgctacatg | gtcatagacc | 540 |
| tcccatgccc | tcctttcggg | cttgcttcaa | gagcatcttc | cgcattcata | cagaaactgg | 600 |
| caacatctgg | acccatctgc | ttggtttcgt | gctgtttctc | ttttgggaa | tcttgaccat | 660 |
| gctcagacca | aatatgtact | tcatggcccc | tctacaggag | aaggtggttt | ttgggatgtt | 720 |
| cttttttggt | gcagtgctct | gcctcagctt | tcctggctc | tttcacaccg | tctattgtca | 780 |
| ttcagagaaa | gtctctcgga | cttttttccaa | actggactat | tcaggattg | ctcttctaat | 840 |
| tatggggagc | tttgtcccct | ggctctatta | ttccttctac | tgctccccac | agccacggct | 900 |
| catctacctc | tccatcgtct | gtgtcctggg | catttctgcc | atcattgtgg | cgcagtggga | 960 |

-continued

```
ccggtttgcc actcctaagc accggcagac aagagcaggc gtgttcctgg gacttggctt    1020
gagtggcgtc gtgccacca tgcactttac tatcgctgag ggctttgtca aggccaccac    1080
agtgggccag atgggctggt tcttcctcat ggctgtgatg tacatcactg gagctggcct    1140
ttatgctgct cgaattcctg agcgcttctt tcctggaaaa tttgacatat ggttccagtc    1200
tcatcagatt ttccatgtcc tggtggtggc agcagccttt gtccacttct atggagtctc    1260
caaccttcag gaattccgtt acggcctaga aggcggctgt actgatgaca cccttctctg    1320
agccttccca cctgcggggt ggaggaggaa cttcccaagt gcttttaaaa ataacttctt    1380
tgctgaagtg agaggaagag tctgagttgt ctgtttctag aagaaacctc ttagagaatt    1440
cagtaccaac caagcttcag cccactttca cacccactgg gcaataaact ttccatttcc    1500
attctcctag ctggggatgg ggcatggtca aacttagcca tcccctcctc agcaaggcat    1560
ctaccggccc ctcacagaga cagtactttg aaactcatgt tgagatttta ccctctcctc    1620
caaccatttt gggaaaatta tggactggga ctcttcagaa attctgtctt ttcttctgga    1680
agaaaatgtc cctcccttac ccccatcctt aactttgtat cctggcttat aacaggccat    1740
ccatttttgt agcacacttt tcaaaaacaa ttatataccc tggtcccatc tttctagggc    1800
ctggatctgc ttatagagca ggaagaataa agccaccaac ttttacctag cccggctaat    1860
catggaagtg tgtccaggct tcaagtaact tgagttttaa ttttttttttt ttcttggcag    1920 agtaatgtaa aatttaaatg gggaaagata tttaatattt aatactaagc tttaaaaga    1980 aacctgctat cattgctatg tatcttgatg caaagactat gatgttaata aagaaagta    2040 cagaagagac ttggcattca aagatttcaa aaaaaaaaaa aaaaaaaaaa aaaaaaaaaa    2100
aaaaaaaa                                                              2108
```

<210> SEQ ID NO 46
<211> LENGTH: 375
<212> TYPE: PRT
<213> ORGANISM: Artificial Sequence
<220> FEATURE:
<223> OTHER INFORMATION: Synthetic construct

<400> SEQUENCE: 46

```
Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Pro Lys Ala
        35                  40                  45

Glu Glu Glu Gln Thr Cys Pro Val Pro Gln Glu Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
            100                 105                 110

Gly His Arg Pro Pro Met Pro Ser Phe Arg Ala Cys Phe Lys Ser Ile
        115                 120                 125

Phe Arg Ile His Thr Glu Thr Gly Asn Ile Trp Thr His Leu Leu Gly
    130                 135                 140

Phe Val Leu Phe Leu Phe Leu Gly Ile Leu Thr Met Leu Arg Pro Asn
145                 150                 155                 160
```

```
Met Tyr Phe Met Ala Pro Leu Gln Glu Lys Val Val Phe Gly Met Phe
            165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
            195                 200                 205

Tyr Ser Gly Ile Ala Leu Leu Ile Met Gly Ser Phe Val Pro Trp Leu
            210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
            245                 250                 255

Arg Phe Ala Thr Pro Lys His Arg Gln Thr Arg Ala Gly Val Phe Leu
            260                 265                 270

Gly Leu Gly Leu Ser Gly Val Val Pro Thr Met His Phe Thr Ile Ala
            275                 280                 285

Glu Gly Phe Val Lys Ala Thr Thr Val Gly Gln Met Gly Trp Phe Phe
            290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
            325                 330                 335

His Gln Ile Phe His Val Leu Val Ala Ala Ala Phe Val His Phe
            340                 345                 350

Tyr Gly Val Ser Asn Leu Gln Glu Phe Arg Tyr Gly Leu Glu Gly Gly
            355                 360                 365

Cys Thr Asp Asp Thr Leu Leu
            370                 375

<210> SEQ ID NO 47
<211> LENGTH: 2072
<212> TYPE: DNA
<213> ORGANISM: Artificial Sequence
<220> FEATURE:
<223> OTHER INFORMATION: Oligonucleotide primer

<400> SEQUENCE: 47
ggggccgctc ggccgcaggc cgcctccagc gccgcgggat gtagcgcggg ggaccgcggc      60
ccccagcaga gcccgcctgc ccggcttgtc taccatcaga gggagatctc tgcccctgg     120 ggctgagaga ccccaacctt tccccaagct gaagctgcag gtattgagg taccagccag     180 atgtcttccc acaaaggatc tgtggtggca caggggaatg ggctcctgc cagtaacagg     240 gaagctgaca cggtggaact ggctgaactg ggacccctgc tagaagagaa gggcaaacgg     300
gtaatcgcca acccacccaa agctgaagaa gagcaaacat gcccagtgcc ccaggaagaa     360
gaggaggagg tgcgggtact gacacttccc ctgcaagccc accacgccat ggagaagatg     420
gaagagtttg tgtacaaggt ctgggaggga cgttggaggg tcatcccata tgatgtgctc     480
cctgactggc taaaggacaa cgactatctg ctacatggtc atagacctcc catgccctcc     540
tttcgggctt gcttcaagag catcttccgc attcatacag aaactggcaa catctggacc     600
catctgcttg gttcgtgct gtttctcttt ttgggaatct tgaccatgct cagaccaaat     660
atgtacttca tggcccctct acaggagaag gtggttttg ggatgttctt tttgggtgca     720
gtgctctgcc tcagcttctc ctggctcttt cacaccgtct attgtcattc agagaaagtc     780
tctcggactt tttccaaact ggactattca gggattgctc ttctaattat ggggagcttt     840
```

```
gtcccctggc tctattattc cttctactgc tccccacagc cacggctcat ctacctctcc    900
atcgtctgtg tcctgggcat ttctgccatc attgtggcgc agtgggaccg gtttgccact   960
cctaagcacc ggcagacaag agcaggcgtg ttcctgggac ttggcttgag tggcgtcgtg  1020
cccaccatgc actttactat cgctgagggc tttgtcaagg ccaccacagt gggccagatg  1080
ggctggttct tcctcatggc tgtgatgtac atcactggag ctggccttta tgctgctcga  1140
attcctgagc gcttctttcc tggaaaattt gacatatggt tccagtctca tcagatttac  1200
catgtcctgg tggtggcagc agcctttgtc cacttctatg gagtctccaa ccttcaggaa  1260
ttccgttacg gcctagaagg cggctgtact gatgacaccc ttctctgagc cttcccacct  1320
gcggggtgga ggaggaactt cccaagtgct tttaaaaata acttctttgc tgaagtgaga  1380
ggaagagtct gagttgtctg tttctagaag aaacctctta gagaattcag taccaaccaa  1440
gcttcagccc actttcacac ccactgggca ataaactttc catttccatt ctcctagctg  1500
gggatgggc atggtcaaac ttagccatcc cctcctcagc aaggcatcta ccggcccctc   1560
acagagacag tactttgaaa ctcatgttga gattttaccc tctcctccaa ccattttggg  1620
aaaattatgg actgggactc ttcagaaatt ctgtcttttc ttctggaaga aaatgtccct  1680
cccttacccc catccttaac tttgtatcct ggcttataac aggccatcca tttttgtagc  1740
acactttca aaacaatta tacccctgg tccatctttt ctagggcctg gatctgctta    1800
tagagcagga agaataaagc caccaacttt tacctagccc ggctaatcat ggaagtgtgt  1860
ccaggcttca gtaacttga gttttaattt ttttttttt cttggcagag taatgtaaaa    1920
tttaaatggg gaagatatt taatatttaa tactaagctt taaaaagaaa cctgctatca   1980
ttgctatgta tcttgatgca aagactatga tgttaataaa agaaagtaca gaagagactt  2040
ggcattcaaa gaaaaaaaaa aaaaaaaaaa aa                                 2072
```

<210> SEQ ID NO 48
<211> LENGTH: 375
<212> TYPE: PRT
<213> ORGANISM: Artificial Sequence
<220> FEATURE:
<223> OTHER INFORMATION: Synthetic construct

<400> SEQUENCE: 48

```
Met Ser Ser His Lys Gly Ser Val Val Ala Gln Gly Asn Gly Ala Pro
1               5                   10                  15

Ala Ser Asn Arg Glu Ala Asp Thr Val Glu Leu Ala Glu Leu Gly Pro
            20                  25                  30

Leu Leu Glu Glu Lys Gly Lys Arg Val Ile Ala Asn Pro Pro Lys Ala
        35                  40                  45

Glu Glu Glu Gln Thr Cys Pro Val Pro Gln Glu Glu Glu Glu Glu Val
    50                  55                  60

Arg Val Leu Thr Leu Pro Leu Gln Ala His His Ala Met Glu Lys Met
65                  70                  75                  80

Glu Glu Phe Val Tyr Lys Val Trp Glu Gly Arg Trp Arg Val Ile Pro
                85                  90                  95

Tyr Asp Val Leu Pro Asp Trp Leu Lys Asp Asn Asp Tyr Leu Leu His
                100                 105                 110

Gly His Arg Pro Pro Met Pro Ser Phe Arg Ala Cys Phe Lys Ser Ile
            115                 120                 125

Phe Arg Ile His Thr Glu Thr Gly Asn Ile Trp Thr His Leu Leu Gly
        130                 135                 140

Phe Val Leu Phe Leu Phe Leu Gly Ile Leu Thr Met Leu Arg Pro Asn
```

```
                145                 150                 155                 160
Met Tyr Phe Met Ala Pro Leu Gln Glu Lys Val Val Phe Gly Met Phe
                165                 170                 175

Phe Leu Gly Ala Val Leu Cys Leu Ser Phe Ser Trp Leu Phe His Thr
            180                 185                 190

Val Tyr Cys His Ser Glu Lys Val Ser Arg Thr Phe Ser Lys Leu Asp
        195                 200                 205

Tyr Ser Gly Ile Ala Leu Leu Ile Met Gly Ser Phe Val Pro Trp Leu
    210                 215                 220

Tyr Tyr Ser Phe Tyr Cys Ser Pro Gln Pro Arg Leu Ile Tyr Leu Ser
225                 230                 235                 240

Ile Val Cys Val Leu Gly Ile Ser Ala Ile Val Ala Gln Trp Asp
                245                 250                 255

Arg Phe Ala Thr Pro Lys His Arg Gln Thr Arg Ala Gly Val Phe Leu
                260                 265                 270

Gly Leu Gly Leu Ser Gly Val Val Pro Thr Met His Phe Thr Ile Ala
            275                 280                 285

Glu Gly Phe Val Lys Ala Thr Thr Val Gly Gln Met Gly Trp Phe Phe
        290                 295                 300

Leu Met Ala Val Met Tyr Ile Thr Gly Ala Gly Leu Tyr Ala Ala Arg
305                 310                 315                 320

Ile Pro Glu Arg Phe Phe Pro Gly Lys Phe Asp Ile Trp Phe Gln Ser
                325                 330                 335

His Gln Ile Tyr His Val Leu Val Val Ala Ala Ala Phe Val His Phe
                340                 345                 350

Tyr Gly Val Ser Asn Leu Gln Glu Phe Arg Tyr Gly Leu Glu Gly Gly
            355                 360                 365

Cys Thr Asp Asp Thr Leu Leu
        370                 375

<210> SEQ ID NO 49
<211> LENGTH: 3500
<212> TYPE: DNA
<213> ORGANISM: Artificial Sequence
<220> FEATURE:
<223> OTHER INFORMATION: Oligonucleotide primer

<400> SEQUENCE: 49
agaatttgtt tgtaaggtat gggaaggtcg gtggcgagtg atccctcatg atgtactacc      60
agactggctc aaggataatg acttcctctt gcatggacac cggcctccta tgccttcttt    120
ccgggcctgt tttaagagca ttttcagaat acacacagaa acaggcaaca tttggacaca    180
tctcttaggt tgtgtatcct tcctgtgcct ggggatcttt tatatgtttc gcccaaatat    240
ctcctttgtg gcccctctgc aagagaaggt ggtctttgga ttattttct taggagccat     300 tctctgcctt tcttttcat ggctcttcca cacagtctac tgccactcag agggggtctc     360
tcggctcttc tctaaactgg attactctgg tattgctctt ctgattatgg aagttttgt     420 tccttggctt tattattctt tctactgtaa tccacaacct tgcttcatct acttgattgt    480
catctgtgtg ctgggcattg cagccattat agtctcccag tgggacatgt ttgccacccc    540
tcagtatcgg ggagtaagag caggagtgtt tttgggccta ggcctgagtg gaatcattcc    600
taccttgcac tatgtcatct cggaggggtt ccttaaggcc gccaccatag ggcagatagg    660
ctggttgatg ctgatggcca gcctctacat cacaggagct gccctgtatg ctgcccggat    720
ccccgaacgc ttttttccctg gcaaatgtga catctggttt cactctcatc agctgtttca    780
```

-continued

```
tatctttgtg gttgctggag cttttgttca cttccatggt gtctcaaacc tccaggagtt      840
tcgtttcatg atcggcgggg gctgcagtga agaggatgca ctgtgatacc taccagtctc      900
cagggactat gaccctaaac cagggcctgc ggcacttgcg ggcctccctg ctggctactg      960
atgccagtac cagaggagcc ccaaaacttt gacagcctcg tgggctttgt gacggcccag     1020
gggctctgcg tggtacatga ctgagaagag aaaaacaaaa ataaatcata cctcaaagga     1080
tggagtgcat caattgggag aaaaggagac atagcccaaa ccctggctta ttcttgggat     1140
ctactgattg cgggctctgc aagacccttg gcaaactggc ttctgatcca tatcatattt     1200
atttgtagaa gatggcgaaa cagtttagct ggtggttctt tcttctccct ttctctctct     1260
ctatgacaat aatacaaacc aatttaagtg aacatttata tccgataagg ggtgggagtg     1320
tgattttaaa tgctcttttg ggagaacaaa gaaattaatg taaataagat ttctaactgt     1380
ttaaataaga ctttatataa atgtttaaaa catagcggta agggagggag ggagaatttt     1440
tgtatagaat gaaacatgca agtaccacac actgtttgaa ttttgcacaa aaagtgactg     1500
taggatcagg tgatagcccc ggaatgtaca gtgtcttggt gcaccaagat gccttctaaa     1560
ggctgacata ccttggaccc taatggggca gagagtatag ccctagccca gtggtgacat     1620
gaccactccc tttgggaggc ctgaggtaga ggggagtggt atgtgttttc tcagtggaag     1680
cagcacatga gtgggtgaca ggatgttaga taaaggctct agttagggtg tcattgtcat     1740
ttgagagact gacacactcc tagcagctgg taaaggggtg ctggaggcca tggaggagct     1800
ctagaaacat tagcatgggc tgatctgatt acttcctggc atcccgctca cctttatggg     1860
aagtcttatt agagggatgg gacagttttc catatccttg ctgtggagct ctggaacact     1920
ctctaaattt ccctctatta aaaatcactg ccctaactat acttcctcct tgagggaata     1980
gaaatggacc tttctctgac atagttcttg gcatgggagc cagccacaaa tgagattctg     2040
acgtgtccag gtttctcctg agctcatcta catagattgg tagacccttc ctttggatta     2100
ggaaagatga gttttacctc tggtacactg tcttggtaag cctggatgtg acagacacct     2160
cggctctcct tgaataagaa agccagcaga actcttaaag ccagttgtag tacggagttg     2220
tcagcactca ctgaacctca ctttacaggg ataagagtg tgtggcattt taaatacaat     2280
ggtatgttat tgccagggag tgaggtacaa gacgatggct catgtcacag gcctacctga     2340
tacggtgtca gagaaagtgg tggggaaagg atctggttca tggaattctg atcttggccc     2400
ataggtgaac caccaaaata gtgctcgagt cttaggttac tgtcatcaaa gacttgggat     2460
gactccatta tatcctgggg ttgtgggtat tagaactaaa tatggaggtc ctgagcatgg     2520
ggactggtgt cctcagtagg tgtttgggaa tatgggaagg gtctcctatt tattcaatag     2580
agttttctca gttattttcc tccctcgccc ttgcaatctc cagcaaaagg tgggatctag     2640
gaagaaagaa tccagtgtag aagttgagaa gaacttgaac gttttggttc tggataaggt     2700
cactgtccta ggtgctaggt ggaccgagca aaagactcag tggatgaact ggtgcagtgc     2760
ctgacagaat aaagaacagt attaatccct ttgagaaagc atagtccagc aggacagtgg     2820
ccatttggac agaagcccac ttagtttctt gggagcaaca gcacgtatca gaagccagac     2880
ttgctcttcg gtcatgcact ttgggataca gcgtataggt gcagccctgt cacaacacca     2940
acagaagtag cagcctctgg gtgcagtcac ccacacccca aagctggaag gatctggttc     3000
aacatagcac aaaccccttag gaaaaatgaa attaacatca ctgatgtgta atccagtaaa     3060
atctcccttt ttcgggtgtg tatgtgggca tgtgcccatt tctatgtgtg tgtctacgtg     3120
cagctcacta ccaacagcct catgtgcact tgacctgaca gtgctcgctg agaactctca     3180
```

```
ccaggttggc gcctgaatgc cttactctca gcagtcagag gcttgcttgc tctgtgcaga    3240 ttttaattt tctttttgg ccctaggctg gttgggacct ctacagcttc attctttcac    3300
attaaatagt gaccttttc agtattttcc ctcttcccct ttataaatta tgctaaagcc    3360
acaaagcaca ttttgggga tcatagaagg ttggggttcc agaaaggcat ctgtgtgatg    3420
gttccattga tgtgggattt ccctacttgc tgtattctca gtttctaata aaagaaccca    3480
aatgaaaaaa aaaaaaaaa                                                 3500
```

<210> SEQ ID NO 50
<211> LENGTH: 386
<212> TYPE: PRT
<213> ORGANISM: Artificial Sequence
<220> FEATURE:
<223> OTHER INFORMATION: Synthetic construct

<400> SEQUENCE: 50

```
Met Asn Glu Pro Thr Glu Asn Arg Leu Gly Cys Ser Arg Thr Pro Glu
1               5                  10                  15

Pro Asp Ile Arg Leu Arg Lys Gly His Gln Leu Asp Gly Thr Arg Arg
            20                  25                  30

Gly Asp Asn Asp Ser His Gln Gly Asp Leu Glu Pro Ile Leu Glu Ala
        35                  40                  45

Ser Val Leu Ser His His Lys Lys Ser Ser Glu Glu His Glu Tyr
    50                  55                  60

Ser Asp Glu Ala Pro Gln Glu Asp Gly Phe Met Gly Met Ser Pro
65                  70                  75                  80

Leu Leu Gln Ala His His Ala Met Glu Lys Met Glu Glu Phe Val Cys
                85                  90                  95

Lys Val Trp Glu Gly Arg Trp Arg Val Ile Pro His Asp Val Leu Pro
            100                 105                 110

Asp Trp Leu Lys Asp Asn Asp Phe Leu Leu His Gly His Arg Pro Pro
        115                 120                 125

Met Pro Ser Phe Arg Ala Cys Phe Lys Ser Ile Phe Arg Ile His Thr
    130                 135                 140

Glu Thr Gly Asn Ile Trp Thr His Leu Leu Gly Cys Val Phe Phe Leu
145                 150                 155                 160

Cys Leu Gly Ile Phe Tyr Met Phe Arg Pro Asn Ile Ser Phe Val Ala
                165                 170                 175

Pro Leu Gln Glu Lys Val Val Phe Gly Leu Phe Phe Leu Gly Ala Ile
            180                 185                 190

Leu Cys Leu Ser Phe Ser Trp Leu Phe His Thr Val Tyr Cys His Ser
        195                 200                 205

Glu Gly Val Ser Arg Leu Phe Ser Lys Leu Asp Tyr Ser Gly Ile Ala
    210                 215                 220

Leu Leu Ile Met Gly Ser Phe Val Pro Trp Leu Tyr Tyr Ser Phe Tyr
225                 230                 235                 240

Cys Asn Pro Gln Pro Cys Phe Ile Tyr Leu Ile Val Ile Cys Val Leu
                245                 250                 255

Gly Ile Ala Ala Ile Ile Val Ser Gln Trp Asp Met Phe Ala Thr Pro
            260                 265                 270

Gln Tyr Arg Gly Val Arg Ala Gly Val Phe Leu Gly Leu Gly Leu Ser
        275                 280                 285

Gly Ile Ile Pro Thr Leu His Tyr Val Ile Ser Glu Gly Phe Leu Lys
    290                 295                 300

Ala Ala Thr Ile Gly Gln Ile Gly Trp Leu Met Leu Met Ala Ser Leu
```

```
                305                 310                 315                 320
Tyr Ile Thr Gly Ala Ala Leu Tyr Ala Ala Arg Ile Pro Glu Arg Phe
                325                 330                 335

Phe Pro Gly Lys Cys Asp Ile Trp Phe His Ser His Gln Leu Phe His
                340                 345                 350

Ile Phe Val Val Ala Gly Ala Phe Val His Phe His Gly Val Ser Asn
                355                 360                 365

Leu Gln Glu Phe Arg Phe Met Ile Gly Gly Gly Cys Ser Glu Glu Asp
        370                 375                 380

Ala Leu
385
```